United States Patent [19]
Bandman et al.

[11] Patent Number: 5,989,860
[45] Date of Patent: Nov. 23, 1999

[54] HUMAN ISOMERASE HOMOLOGS

[75] Inventors: Olga Bandman; Jennifer L. Hillman, both of Mountain View; Karl J. Guegler, Menlo Park; Neil C. Corley, Mountain View; Purvi Shah, Sunnyvale, all of Calif.

[73] Assignee: Incyte Pharmaceuticals, Inc., Palo Alto, Calif.

[21] Appl. No.: 08/989,386

[22] Filed: Dec. 12, 1997

[51] Int. Cl.$^6$ .............................. C12P 21/06; C12Q 1/68; C07H 21/02
[52] U.S. Cl. .............................. 435/69.1; 435/6; 435/320; 536/23.1
[58] Field of Search ........................... 530/350; 536/23.5, 536/23.1; 435/326, 252.3, 69.1, 6, 320

[56] References Cited

PUBLICATIONS

Burgess et al. T. Cell Biol. 11: 2129–2138, 1990.
Lazar et al. Mol. Cell Biol. 8: 1247–1252, 1988.
Tao et al. J. Immunol. 143(8) 2595–2601, 1989.
Grillies et al. Human Antibodies a Hylenidomas, 1990 1(1):47–54.
Simek, SL et al. Gen Barck. Accession No. L 070 63 $_7$in MPSRCH Search, 1993.
Coss, MC et al. Gen Barck. Accession No. L07063 in MPSRCH search, 1995.
McDonald, M et al. Gen Barck—Accession No. Z56231, 1995.
Cross, SH et al. Gen Barck. Accession No. Z56231, 1994.
Watson, et al. Mol. Biol. of the Gene, pp. 1074–1075, 1987.
Samibrook et al. Mol. cloning pp. 1.72, 1.73, 1.75, 16.3, 16.4, 1989.
Bergsma, D.J. et al., "The Cyclophilin Multigene Family of Peptidyl–Prolyl Isomerases" *J.Biol.Chem.* (1991) 266:23204–23214.
Coss, M.C. et al., "Molecular Cloning, DNA Sequence Analysis, and Biochemical Characterization of a Novel 65–KDa FK506–binding Protein (FKBP65)" *J.Biol.Chem.* (1995) 270:29336–29341.
Schreiber, Stuart L. "Chemistry and Biology of the Immunophilins and Their Immunosuppressive Ligands" *Science* (1991) 251:283–287.
Roper, D.I. and Cooper, R.A. "Purification, necleotide sequence and some properties of a bifunctional isomerase/decarboxylase from the homoprotocatechuate degradative pathway of *Escherichia coli* C" *Eur.J.Biochem.* (1993) 217:575–580.
Simek, S.L. et al., (GI 894162), GenBank Sequence Database (Accession L07063), National Center for Biotechnology Information, National Library of Medicine, Bethesda, Maryland, 20894.
Davis, R.E. et al., (GI 2190533), GenBank Sequence Database (Accession U30265), National Center for Biotechnology Information, National Library of Medicine, Bethesda, Maryland, 20894.
Davis, R.E. et al., (GI 2190532), GenBank Sequence Database (Accession U30265), National Center for Biotechnology Information, National Library of Medicine, Bethesda, Maryland, 20894.
Bult, C.J. et al., (GI 1500558), GenBank Sequence Database (Accession U67606), National Center for Biotechnology Information, National Library of Medicine, Bethesda, Maryland, 20894.
Rahfeld, J.U., et al., "Confirmation of the existence of a third family among peptidyl–prolyl cistrans isomerases amino acid sequence and recombinant production of parvulin." *FEBS Letters* (1994) 352:180–184.
Jenkins, J.R. and Cooper, R.A. "Molecular Cloning, Expression, and Analysis of the Genes of the Homoprotocatechuate Catabolic Pathway of *Escherichia coli* C" *J.Bacteriol.* (1988) 170:5317–5324.
Bult, C.J. et al., (GI 2826444), GenBank Sequence Database (Accession U67606 and L77117), National Center for Biotechnology Information, National Library of Medicine, Bethesda, Maryland, 20894.

*Primary Examiner*—Paula K. Hutzell
*Assistant Examiner*—Lin Sun-Hoffman
*Attorney, Agent, or Firm*—Incyte Pharmaceuticals, Inc.

[57] ABSTRACT

The invention provides human isomerase homologs (HIH) and polynucleotides which identify and encode HIH. The invention also provides expression vectors, host cells, antibodies, agonists, and antagonists. The invention also provides methods for treating or preventing disorders associated with expression of HIH.

10 Claims, 20 Drawing Sheets

```
5' CAA CTC CCT CGC TCG CCC TCA CTG CCG GCG GTC CCA ACT CCA GGC ACC ATG TTC      54
                                                                        M   F

CCC GCG GGC CCC CCC AGC CAC AGC CTC CTC CGG CTC CCC CTG CAG TTG CTG        108
     P   A   G   P   P   S   H   S   L   L   R   L   P   L   Q   L   L

CTA CTG GTG GTG CAG GCC GTG GGG CTG AGG GGG CTG GGC CGC GCC CCG GCC GGG    162
     L   L   V   V   Q   A   V   G   L   R   G   L   G   R   A   P   A   G

GGC CCC CTG GAA GAT GTG GTC ATC GAG AGG TAC CAC ATC CCC AGG GCC TGT CCC    216
     G   P   L   E   D   V   V   I   E   R   Y   H   I   P   R   A   C   P

CGG GAA GTG CAG ATG GGG GAT TTT GTG TCA AGC CGC TAC AAC ACT TTT GAA        270
     R   E   V   Q   M   G   D   F   V   S   S   R   Y   N   T   F   E

GAT GGC AAG AAG TTT GAT TCA AGC TAT GAT CGC AAC ACC TTG GTG GCC ATC GTG    324
     D   G   K   K   F   D   S   S   Y   D   R   N   T   L   V   A   I   V

GTG GGT GGG CGC CTC ATC ACT GGC ATG GAC CGA GGC CTC ATG GGC ATG TGT        378
     V   G   G   R   L   I   T   G   M   D   R   G   L   M   G   M   C
```

FIGURE 1A

```
       387            396            405            414            423            432
GTC AAC GAG CGG CGA CGC CTC ATT GTG CCT CCC CAC CTG GGC TAT GGG AGC ATC
 V   N   E   R   R   R   L   I   V   P   P   H   L   G   Y   G   S   I 441            450            459            468            477            486
GGC CTG GCG GGG CTC ATT CCA CCG GAT GCC ACC CTC TAC TTC GAT GTG GTT CTG
 G   L   A   G   L   I   P   P   D   A   T   L   Y   F   D   V   V   L 495            504            513            522            531            540
CTG GAT GTG TGG AAC AAG GAA GAC GCC ACC GTG CAG AGC ACA TTG CTG CGC CCG
 L   D   V   W   N   K   E   D   A   T   V   Q   S   T   L   L   R   P 549            558            567            576            585            594
CCC CAC TGC CCC CGC ATG GTC CAG GAC GGC GAC ACC TCC TTT GTC CGC TAC AAT
 P   H   C   P   R   M   V   Q   D   G   D   T   S   F   V   R   Y   N 603            612            621            630            639            648
GGC ACC CTG CTG GAC ACC TCC TTC GAC ACC AGC TAC AAG GGC GGC ACT
 G   T   L   L   D   G   T   S   F   D   T   S   Y   K   G   G   T 657            666            675            684            693            702
TAT GAC ACC TAC GTC GGC TCT GGT TGG CTG ATC AAG GGC ATG GAC CAG GGG CTG
 Y   D   T   Y   V   G   S   G   W   L   I   K   G   M   D   Q   G   L 711            720            729            738            747            756
CTG GGC ATG TGT CCT GGA GAG AGA AGG AAG ATT ATC CCT CCA TTC CTG GCC
 L   G   M   C   P   G   E   R   R   K   I   I   P   P   F   L   A
```

FIGURE 1B

```
                 765       774       783       792       801       810
TAT GGC GAG AAA GGC TAT GGG ACA GTG ATC CCC CAG GCC TCG CTG GTC TTT
 Y   G   E   K   G   Y   G   T   V   I   P   Q   A   S   L   V   F 819       828       837       846       855       864
CAC GTC CTC CTG ATT GAC GTG CAC AAC CCG AAG GAC GCT GTC CAG CTA GAG ACG
 H   V   L   L   I   D   V   H   N   P   K   D   A   V   Q   L   E   T 873       882       891       900       909       918
CTG GAG CTC CCC CCC GGC TGT GTC CGC AGA GCC GGG ACC TTC GAT TTC ATG CGC
 L   E   L   P   P   G   C   V   R   R   A   G   T   F   D   F   M   R 927       936       945       954       963       972
TAC CAC TAC AAT GGC TCC TTG ATG GAC GGC ACC CTC TTC GAT TCC AGC TAC TCC
 Y   H   Y   N   G   S   L   M   D   G   T   L   F   D   S   S   Y   S 981       990       999       1008      1017      1026
CGC AAC CAC ACC TAC AAT ACC TAT ATC GGG CAG GGT TAC ATC CCC GGG ATG
 R   N   H   T   Y   N   T   Y   I   G   Q   G   Y   I   P   G   M 1035      1044      1053      1062      1071      1080
GAC CAG GGG CTG CAG GGT GCC TGC ATG GGG GAA CGC CGG AGA ATT ACC ATC CCC
 D   Q   G   L   Q   G   A   C   M   G   E   R   R   R   I   T   I   P 1089      1098      1107      1116      1125      1134
CCG CAC CTC GCC TAT GGG GAG AAT GGA ACT GGA GAC AAG ATC CCT GGC TCT GCC
 P   H   L   A   Y   G   E   N   G   T   G   D   K   I   P   G   S   A

FIGURE 1C
```

```
      1143        1152        1161        1170        1179        1188
GTG CTA ATC TTC AAC GTC CAT GTC ATT GAC TTC CAC AAC CCT GCG GAT GTG GTG
 V   L   I   F   N   V   H   V   I   D   F   H   N   P   A   D   V   V 1197        1206        1215        1224        1233        1242
GAA ATC AGG ACA CTG TCC CGG CCA TCT GAG ACC TGC AAT GAG ACC ACC AAG CTT
 E   I   R   T   L   S   R   P   S   E   T   C   N   E   T   T   K   L 1251        1260        1269        1278        1287        1296
GGG GAC TTT GTT CGA TAC CAT TAC AAC TGT TCT TTG CTG GAC ACC GGC CAG CTG
 G   D   F   V   R   Y   H   Y   N   C   S   L   L   D   T   G   Q   L 1305        1314        1323        1332        1341        1350
TTC ACC TCG CAT GAC TAC GGG GCC CCC CAG GAG GCG ACT CTC GGG GCC AAC AAG
 F   T   S   H   D   Y   G   A   P   Q   E   A   T   L   G   A   N   K 1359        1368        1377        1386        1395        1404
GTG ATC GAA GGC CTG GAC ACG GGC CTG CAG GGC ATG TGT GTG GGA GAG AGG CGG
 V   I   E   G   L   D   T   G   L   Q   G   M   C   V   G   E   R   R 1413        1422        1431        1440        1449        1458
CAG CTC ATC GTG CCC CCG CAC CTG GCC CAC GGG GAG AGT GGA GCC CGG GGA GTC
 Q   L   I   V   P   P   H   L   A   H   G   E   S   G   A   R   G   V 1467        1476        1485        1494        1503        1512
CCA GGC AGT GCT GTG CTG CTG TTT GAG GTG GAG CTG GTG TCC CGG GAG GAT GGG
 P   G   S   A   V   L   L   F   E   V   E   L   V   S   R   E   D   G
```

FIGURE 1D

```
      1521            1530            1539            1548            1557            1566
CTG CCC ACA GGC TAC CTG TTT GTG TGG CAC AAG GAC CCT CCT GCC AAC CTG TTT
 L   P   T   G   Y   L   F   V   W   H   K   D   P   P   A   N   L   F 1575            1584            1593            1602            1611            1620
GAA GAC ATG GAC CTC AAC AAG GAT GGC GAG GTC CCT CCG GAG TTC TCC ACC
 E   D   M   D   L   N   K   D   G   E   V   P   P   E   F   S   T 1629            1638            1647            1656            1665            1674
TTC ATC AAG GCT CAA GTG AGT GAG GGC AAA GGA CGC CTC ATG CCT GGG CAG GAC
 F   I   K   A   Q   V   S   E   G   K   G   R   L   M   P   G   Q   D 1683            1692            1701            1710            1719            1728
CCT GAG AAA ACC ATA GGA GAC ATG TTC CAG AAC CAG GAC CGC AAC CAG GAC GGC
 P   E   K   T   I   G   D   M   F   Q   N   Q   D   R   N   Q   D   G 1737            1746            1755            1764            1773            1782
AAG ATC ACA GTC GAC GAG CTC AAG TCA GAT GAG GAC GAG CGG GTC
 K   I   T   V   D   E   L   K   S   D   E   D   E   R   V 1791            1800            1809            1818            1827            1836
CAC GAG GAG CTC TGA GGG GCA GGG AGC AGG CCT GAG ACA CAG AGG CCC
 H   E   E   L 1845            1854            1863            1872            1881            1890
ACT GCG AGG GGG ACA GTG GCG GTG GGA CTG ACC TGC TGA CAG TCA CCC TCC CTC
```

FIGURE 1E

```
     1899      1908      1917      1926      1935      1944
TGC TGG GAT GAG GTC CAG GAG CCA ACT AAA ACA ATG GCA GAG GAG ACA TCT CTG
     1953      1962      1971      1980      1989      1998
GTG TTC CCA CCA CCC TAG ATG AAA ATC CAC AGC ACA GAC CTC TAC CGT GTT TCT
     2007      2016      2025      2034      2043      2052
CTT CCA TCC CTA AAC CAC TTC CTT AAA ATG TTT GGA TTT GCA AAG CCA ATT TGG
     2061      2070      2079      2088      2097      2106
GGC CTG TGG AGC CTG GGG TTG GAT AGG GCC ATG GCT GGT CCC CCA CCA TAC CTC
     2115      2124      2133      2142      2151      2160
CCC TCC ACA TCA CTG ACA CAG CTG AGC TTG TTA TCC ATC TCC CCA AAC TTT CTC
     2169      2178      2187      2196      2205      2214
TTT CTT TGT ACT TCT TGT CAT CCC CAC TCC CAG CCC CTA TTC CTC TAT GTG ACA
     2223      2232      2241      2250      2259      2268
GCT GGC TAG GAC CCC TCT GCC TTC CTC CCC AAT CCT GAC TGG CTC CTA GGG AAG
     2277      2286      2295      2304      2313      2322
GGG AAG GCT CCT GGA GGG CAG CCC TAC CTC TCC CAT GCC CTT TGC CCT CCT CCC
     2331      2340      2349      2358      2367      2376
TCG CCT CCA GTG GAG GCT GAG CTG ACC CTG GGC TGC TGG AGG CCA GAC TGG GCT
```

FIGURE 1F

```
      2385           2394           2403           2412           2421           2430
GTA GTT AGC TTT TCA TCC CTA AAG AAG GCT TTC CCT AAG GAA CCA TAG AAG AGA
      2439           2448           2457           2466           2475           2484
GGA AGA AAA CAA AGG GCA TGT GTG AGG GAA GCT GCT TGG GTG GGT GTT AGG GCT
      2493           2502           2511           2520           2529           2538
ATG AAA TCT TGG ATT TGG GGC TGA GGG GTG GGA GGG AGG GCA GAG CTC TGC ACA
      2547           2556           2565           2574           2583           2592
CTC AAA GGC TAA ACT GGT GTC AGT CCT TTT TTC CTT TGT TCC AAA TAA AAG ATT
      2601           2610
AAA CCA AAA AAA AAA AAA 3'
```

FIGURE 1G

```
                    10              19          28          37          46          55
5'A CAG TGG GGA AGA GGA CGG GTC GAG TGG CTT CCG GCG AAG CGC GCG AGC
                    64              73          82          91          100         109
AAG ATG GCC ACC ACC AAG CGC GTC TTG TAC GTG GGT GGA CTG GCA GAG GAA GTG
    M   A   T   T   K   R   V   L   Y   V   G   G   L   A   E   E   V
                    118             127         136         145         154         163
GAC GAC AAA GTT CTT GAT CAT GCT GCG TTC ATT CCT TTT GGA GAC ATC ACA GAT ATT
D   D   K   V   L   D   H   A   A   F   I   P   F   G   D   I   T   D   I
                    172             181         190         199         208         217
CAG ATT CCT CTG GAT TAT GAA ACA GAA AAG CAC CGA GGA TTT GCT TTT GTT GAA
Q   I   P   L   D   Y   E   T   E   K   H   R   G   F   A   F   V   E
                    226             235         244         253         262         271
TTT GAG TTG GCA GAG GAT GCT GCA GCA GAA AAC ATG ATC GAC AAC ATG AAT GAA TCT GAG
F   E   L   A   E   D   A   A   A   E   N   M   I   D   N   M   N   E   S   E
                    280             289         298         307         316         325
CTT TTT GGA CGT ACA ATT CGT GTC AAT TTG GCC ATC AAA CCA ATG AGA ATT AAG GAA
L   F   G   R   T   I   R   V   N   L   A   I   K   P   M   R   I   K   E
                    334             343         352         361         370         379
GGC TCT TCC AGG CCA GTT TGG TCA GAT GAT GAC TGG TTG AAG TTT TCT GGG
G   S   S   R   P   V   W   S   D   D   D   W   L   K   F   S   G
```

FIGURE 2A

```
        388         397         406         415   424         433
AAG ACG CTT GAA GAG AAT AAA GAG GAA GGG TCA GAG CCT AAA GCA GAG
 K   T   L   E   E   N   K   E   E   G   S   E   P   K   A   E 442         451         460   469         478         487
ACC CAG GAG GGA GAG ATT GCT AAA AAG GCC CGC TCA AAT CCT CAG GTG TAC
 T   Q   E   G   E   I   A   K   K   A   R   S   N   P   Q   V   Y 496         505         514         523   532         541
ATG GAC ATC AAG ATT CCC GGG AAC AAG CCG GCT GGC ATC CGC ATG CTC CGT
 M   D   I   K   I   P   G   N   K   P   A   G   I   R   M   L   R 550         559         568         577   586         595
TCT GAT GTC GTG CCC ATG ACA GCA GAG AAT TTC CGC TGC CTG ACT CAT GAA
 S   D   V   V   P   M   T   A   E   N   F   R   C   L   T   H   E 604         613         622         631   640         649
AAG GGC TTT GGC TTT AAG GGA AGC TTC CAC CGC ATC ATC CCC CAG TTC ATT
 K   G   F   G   F   K   G   S   F   H   R   I   I   P   Q   F   I 658         667         676         685   694         703
TGC CAG AGT GAT TTC ACA AAC CAC GGT GGC ACC AGG GGT CTG CGC AGG CAT
 C   Q   S   D   F   T   N   H   G   G   T   R   G   L   R   R   H 712         721         730         739   748         757
GGC ACT AAG TGT CCC ATG GCA CAT TTG GCC CTC ATG GAG GCC TCA AAA GGG CAG
 G   T   K   C   P   M   A   H   L   A   L   M   E   A   S   K   G   Q
```

FIGURE 2B

```
      766              775              784              793              802              811
GAC CAG CAC CCT CTT CTA CGG AGG AAG GAA CGG GCA CAG CAG GGT GAG CCA CTG
 D   Q   H   P   L   L   R   R   K   E   R   A   Q   Q   G   E   P   L 820              829              838              847              856              865
CGC CTG ATC AAG GCA TCA CCG TTG AAC CTC CTA AGA GGA AAA CAT AAG GCT GTG
 R   L   I   K   A   S   P   L   N   L   L   R   G   K   H   K   A   V 874              883              892              901              910              919
CAA TAC CAG GAA CTG GGA TTC TAG GTT GCC CCA GAT ACC AAG GCA TCA AAA GCC
 Q   Y   Q   E   L   G   F 928              937              946              955              964              973
AGG GGA TCC AGA AAA AAC AAA GAT GGC CAA GAG AGA AAC TGG GGG AAA AGC CAA 982              991             1000             1009             1018             1027
AAG GTT GAG AGC CAC ACC ATC TAG AAG CTT CCT GCC TGC GGT GCG GCA CAG AAA 1036             1045             1054             1063             1072             1081
CAA GGA GAG TCA GCA ATT ACC AGC CAG CCG AGG TCC TGG AAG CTG ACG TAG AGC 1090             1099             1108             1117             1126             1135
TCG TGC CGA CGG CAG ACC TGC CGG CCG TGG GAG CCG CGG ACG TCA TCT GCA GGG 1144             1153             1162             1171             1180             1189
ACA GAA GGG GCA AGG TCT TTT CTG GGG TTC CTG CTG TGT GCA GCT ACT ATG GGG
```

FIGURE 2C

```
      1198         1207         1216         1225         1234         1243
TAC CAG GGT GGA TGC CCT GAT GAG CAC ATT TGT CAA ATA AAT GAA TGA CAG
      1252         1261
GAA ACC AAG AAA AAA AAA A 3'
```

```
5'
                9               18              27              36              45              54
    ATG ACG CAG TTC CTA GAG CAG GGA GAG CAG GCC ACC CTC TCA GTG GCA AGA AGA GCC
     M   T   Q   F   L   E   Q   G   E   Q   A   T   L   S   V   A   R   R   A 63              72              81              90              99             108
    CTG GCT GCC CAG TTG CCA GTC CTA CCA CGG TCG GAG GTA ACC TTC CTG GCT CCA
     L   A   A   Q   L   P   V   L   P   R   S   E   V   T   F   L   A   P 117             126             135             144             153             162
    GTC ACA CGA CCA GAT AAG GTG GTG TGT GTG GGC ATG AAT TAT GTG GAC CAC TGC
     V   T   R   P   D   K   V   V   C   V   G   M   N   Y   V   D   H   C 171             180             189             198             207             216
    AAA GAA CAG AAC GTG CCC GTG CCC AAG GAG CCC ATC ATC TTC AGC AAG TTT GCC
     K   E   Q   N   V   P   V   P   K   E   P   I   I   F   S   K   F   A 225             234             243             252             261             270
    AGC TCC ATC GTG GGG CCC TAT GAT GAG GTG GTC CTC CCA CCA CCA CCA CAG AGC GAG
     S   S   I   V   G   P   Y   D   E   V   V   L   P   P   P   Q   S   E 279             288             297             306             315             324
    GTA GAT TGG GAA GTG GAG CTG GCC GTG GTC ATT GGA AAG AAA GGC AGC CAG CAC ATC
     V   D   W   E   V   E   L   A   V   V   I   G   K   K   G   S   Q   H   I 333             342             351             360             369             378
    AAG GCC ACA GAT GCT ATG GCC CAC GTG GCC GGC TTC ACT GTG GCT CAT GAC GTG
     K   A   T   D   A   M   A   H   V   A   G   F   T   V   A   H   D   V
```

```
AGT GCT CGT GAC TGG CTA ACA AGA CGC AAT GGG AAA CAG TGG CTG CTG GGA AAA
 S   A   R   D   W   L   T   R   R   N   G   K   Q   W   L   L   G   K
387         396         405         414         423         432

ACC TTC GAC ACC TTC TGC CCN CTG GGC CCT GCC TTG GTG ACC AAG GAC AGT GTA
 T   F   D   T   F   C   P   L   G   P   A   L   V   T   K   D   S   V
441         450         459         468         477         486

GCA GAT CCA CAC AAC TTA AAG ATC TGC CGA GTG AAT GGG GAA GTG GTC CAG
 A   D   P   H   N   L   K   I   C   R   V   N   G   E   V   V   Q
495         504         513         522         531         540

AGC GGC AAC ACC AAC CAG ATG GTA CCA TTC AAG ACA GAG GAC CTG ATA TGG GTC
 S   G   N   T   N   Q   M   V   P   F   K   T   E   D   L   I   W   V
549         558         567         576         585         594

TCC CAG TTT GTT ACC TTT TAC CCA GGG GAT GTC ATC CTA ACT GCC TGG CCC CCA
 S   Q   F   V   T   F   Y   P   G   D   V   I   L   T   A   W   P   P
603         612         621         630         639         648

GGT GTC GGT GTA TTC AGG AAA CCT CCT GTC TTT CTC AAG AAG AAG GGG GAT GAA GTC
 G   V   G   V   F   R   K   P   P   V   F   L   K   K   K   G   D   E   V
657         666         675         684         693         702
```

FIGURE 3B

```
     711         720         729         738         747         756
CAG TGT GAG ATT GAA GAA CTA GGT GTC ATC ATC AAC AAG GTG TGA TGG CTC
 Q   C   E   I   E   E   L   G   V   I   I   N   K   V 765         774
CTG CAC AGG CCC TGC ACA TAG 3'
```

HUMAN ISOMERASE HOMOLOGS

FIELD OF THE INVENTION

This invention relates to nucleic acid and amino acid sequences of human isomerase homolog-1, human isomerase homolog-2, and human isomerase homolog-3, and to the use of these sequences in the diagnosis, treatment, and prevention of cancer and immune disorders.

BACKGROUND OF THE INVENTION

Numerous essential biochemical reactions involve the isomerization of a substrate. Enzymes which catalyze such reactions are known as isomerases. A number of isomerases are involved in catalyzing steps in a wide variety of biochemical pathways including protein folding, phototransduction, and various anabolic and catabolic pathways (e.g., glycolysis), in organisms ranging from bacteria to human.

One class of isomerases includes peptidyl-prolyl cis/trans isomerases (PPIases). PPIases catalyze the cis to trans isomerization of certain proline imidic bonds in proteins. Two families of PPIases are the cyclophilins (CyPs), and the FK506 binding proteins (FKBPs). CyP was characterized originally as the receptor for the immunosuppressant drug cyclosporin, an inhibitor of T-cell activation. Subsequent work demonstrated that CyPs isomerase activity is essential for correct protein folding. Thus, the peptidyl-prolyl isomerase activity of CyP may be part of the signaling pathway that leads to T-cell activation (Bergsma, D. J. et al (1991) J. Biol. Chem. 266:23204–14).

There are five members of the FKBP family which are named according to their calculated molecular masses (FKBP12, FKBP13, FKBP25, FKBP52, and FKBP65), and are localized to different regions of the cell where they associate with different protein complexes. FKBP12 is localized to the cytoplasm and is associated with the ryanodine receptor and the inositol 1,4,5-trisphosphate receptor. FKBP 13 is located in the endoplasmic reticulum where it's PPIase activity assists in folding growing polypeptide chains. FKBP25 is found in the nucleus and associates with nucleolin and casein kinase II. FKBP52 associates with unactivated steroid receptors. FKBP65 has been localized to the membrane, but no proteins have yet been shown to interact with it. FKBPs bind the potent immunosuppressants FK506 and rapamycin, thereby inhibiting signaling pathways in T-cells. Specifically, the PPIase activity of FKBPs is inhibited by binding FK506 or rapamycin (Coss, M. et al. (1995) J. Biol. Chem. 270:29336–41; Schreiber, S. L. (1991) Science 251:283–7).

Other isomerases are involved in essential biochemical reaction pathways. For example, in *E. coli*, 3,4-dihydroxyphenylacetate is converted to succinic semialdehyde in an aromatic catabolism pathway known as the homoprotocatechuate pathway. This pathway requires two isomerization steps. The first step is the conversion of 5-carboxymethyl-2-hydroxymuconic acid to 5-oxo-pent-3-ene-1,2,5-tricarboxylic acid by the action of 5-carboxymethyl-2-hydroxymuconate isomerase. In the second step, the enzyme 2-hydroxyhepta-2,4-diene-1,7-dioate isomerase (HHDDI) catalyzes the isomerization of 2hydroxy-hepta-2,4-diene-1,7-dioic acid into 2-oxo-hepta-3-ene-1,7-dioic acid. These isomerization steps are essential to the breakdown of aromatic compounds which produces substrates for energy metabolism (Roper, D. I. and Cooper, R. A. (1993) Eur. J. Biochem. 217: 575–80).

The discovery of new human isomerase homologs and the polynucleotides encoding them satisfies a need in the art by providing new compositions which are useful in the diagnosis, treatment, and prevention of cancer and immune disorders.

SUMMARY OF THE INVENTION

The invention features substantially purified polypeptides, human isomerase homologs, referred to collectively as "HIH" and individually as "HIH-1", "HIH-2", and "HIH-3." In one aspect, the invention provides a substantially purified polypeptide, HIH, comprising an amino acid sequence selected from the group consisting of SEQ ID NO:1, SEQ ID NO:3, SEQ ID NO:5, a fragment of SEQ ID NO:1, a fragment of SEQ ID NO:3, and a fragment of SEQ ID NO:5.

The invention further provides a substantially purified variant of HIH having at least 90% amino acid identity to the amino acid sequences of SEQ ID NO:1, SEQ ID NO:3 or SEQ ID NO:5, or to a fragment of any of these sequences. The invention also provides an isolated and purified polynucleotide sequence encoding the polypeptide comprising an amino acid sequence selected from the group consisting of SEQ ID NO:1, SEQ ID NO:3, SEQ ID NO:5, a fragment of SEQ ID NO:1, a fragment of SEQ ID NO:3, and a fragment of SEQ ID NO:5. The invention also includes an isolated and purified polynucleotide variant having at least 90% polynucleotide identity to the polynucleotide sequence encoding the polypeptide comprising an amino acid sequence selected from the group consisting of SEQ ID NO:1, SEQ ID NO:3, SEQ ID NO:5, a fragment of SEQ ID NO:1, a fragment of SEQ ID NO:3, and a fragment of SEQ ID NO:5.

Additionally, the invention provides a composition comprising a polynucleotide sequence encoding the polypeptide comprising the amino acid sequence selected from the group consisting of SEQ ID NO:1, SEQ ID NO:3, SEQ ID NO:5, a fragment of SEQ ID NO:1, a fragment of SEQ ID NO:3, and a fragment of SEQ ID NO:5. The invention further provides an isolated and purified polynucleotide sequence which hybridizes under stringent conditions to the polynucleotide sequence encoding the polypeptide comprising an amino acid sequence selected from the group consisting of SEQ ID NO:1, SEQ ID NO:3, SEQ ID NO:5, a fragment of SEQ ID NO:1, a fragment of SEQ ID NO:3, and a fragment of SEQ ID NO:5, as well as an isolated and purified polynucleotide sequence which is complementary to the polynucleotide sequence encoding the polypeptide comprising the amino acid sequence selected from the group consisting of SEQ ID NO:1, SEQ ID NO:3, SEQ ID NO:5, a fragment of SEQ ID NO:1, a fragment of SEQ ID NO:3, and a fragment of SEQ ID NO:5.

The invention also provides an isolated and purified polynucleotide sequence comprising a polynucleotide sequence selected from the group consisting of SEQ ID NO:2, SEQ ID NO:4, SEQ ID NO:6, a fragment of SEQ ID NO:2, a fragment of SEQ ID NO:4, and a fragment of SEQ ID NO:6. The invention further provides an isolated and purified polynucleotide variant having at least 90% polynucleotide identity to the polynucleotide sequence comprising a polynucleotide sequence selected from the group consisting of SEQ ID NO:2, SEQ ID NO:4, SEQ ID NO:6, a fragment of SEQ ID NO:2, a fragment of SEQ ID NO:4, and a fragment of SEQ ID NO:6, as well as an isolated and purified polynucleotide sequence which is complementary to the polynucleotide sequence comprising a polynucleotide sequence selected from the group consisting of SEQ ID NO:2, SEQ ID NO:4, SEQ ID NO:6, a fragment of SEQ ID NO:2, a fragment of SEQ ID NO:4, and a fragment of SEQ ID NO:6.

The invention further provides an expression vector containing at least a fragment of the polynucleotide sequence encoding the polypeptide comprising an amino acid sequence selected from the group consisting of SEQ ID NO:1, SEQ ID NO:3, SEQ ID NO:5, a fragment of SEQ ID NO:1, a fragment of SEQ ID NO:3, and a fragment of SEQ ID NO:5. In another aspect, the expression vector is contained within a host cell.

The invention also provides a method for producing a polypeptide comprising the amino acid sequence of SEQ ID NO:1, SEQ ID NO:3, SEQ ID NO:5, a fragment of SEQ ID NO:1, a fragment of SEQ ID NO:3, and a fragment of SEQ ID NO:5, the method comprising the steps of: (a) culturing the host cell containing an expression vector containing at least a fragment of a polynucleotide sequence encoding HIH under conditions suitable for the expression of the polypeptide; and (b) recovering the polypeptide from the host cell culture.

The invention also provides a pharmaceutical composition comprising a substantially purified HIH having the amino acid sequence of SEQ ID NO:1, SEQ ID NO:3, SEQ ID NO:5, a fragment of SEQ ID NO:1, a fragment of SEQ ID NO:3, and a fragment of SEQ ID NO:5 in conjunction with a suitable pharmaceutical carrier.

The invention further includes a purified antibody which binds to a polypeptide comprising the amino acid sequence of SEQ ID NO:1, SEQ ID NO:3, SEQ ID NO:5, a fragment of SEQ ID NO:1, a fragment of SEQ ID NO:3, and a fragment of SEQ ID NO:5, as well as a purified agonist and a purified antagonist to the polypeptide.

The invention also provides a method for treating or preventing a cancer, the method comprising administering to a subject in need of such treatment an effective amount of an antagonist of HIH.

The invention also provides a method for treating or preventing an immune disorder, the method comprising administering to a subject in need of such treatment an effective amount of an antagonist of HIH.

The invention also provides a method for detecting a polynucleotide encoding HIH in a biological sample containing nucleic acids, the method comprising the steps of: (a) hybridizing the complement of the polynucleotide sequence encoding the polypeptide comprising SEQ ID NO:1, SEQ ID NO:3, a fragment of SEQ ID NO:1, or a fragment of SEQ ID NO:3 to at least one of the nucleic acids of the biological sample, thereby forming a hybridization complex; and (b) detecting the hybridization complex, wherein the presence of the hybridization complex correlates with the presence of a polynucleotide encoding HIH in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, 1E, 1F, and 1G show the amino acid sequence (SEQ ID NO:1) and nucleic acid sequence (SEQ ID NO:2) of HIH-1.

FIGS. 2A, 2B, 2C, and 2D show the amino acid sequence (SEQ ID NO:3) and nucleic acid sequence (SEQ ID NO:4) of HIH-2.

FIGS. 3A, 3B, and 3C show the amino acid sequence (SEQ ID NO:5) and nucleic acid sequence (SEQ ID NO:6) of HIH-3.

The alignments were produced using MacDNASIS PRO™ software (Hitachi Software is Engineering Co. Ltd., San Bruno, Calif.).

FIGS. 4A, 4B, and 4C show the amino acid sequence alignment between HIH-1 (2255114; SEQ ID NO:1), and FKBP65 (GI 894162; SEQ ID NO:7).

FIGS. 5A and 5B show the amino acid sequence alignment between HIH-2 (292808; SEQ ID NO:3) and CyP (GI 2190533, SEQ ID NO:8).

FIG. 6 shows the amino acid sequence alignment between HIH-3 (1419071; SEQ ID NO:5) and HHDDI (GI 1500558, SEQ ID NO:9).

The alignments were produced using the multisequence alignment program of DNASTAR software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"HIH," as used herein, refers to the amino acid sequences of substantially purified HIH obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HIH, increases or prolongs the duration of the effect of HIH. Agonists may include proteins, nucleic acids, carbohydrates, or any other molecules which bind to and modulate the effect of HIH.

An "allele" or an "allelic sequence," as these terms are used herein, is an alternative form of the gene encoding HIH. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HIH, as described herein, include those sequences with deletions, insertions, or substitutions of different nucleotides, resulting in a polynucleotide the same HIH or a polypeptide with at least one functional characteristic of HIH. Included within this definition are polymorphisms which may or may not be readily detectable using a particular oligonucleotide probe of the polynucleotide encoding HIH, and improper or unexpected hybridization to alleles, with a locus other than the normal chromosomal locus for the polynucleotide sequence encoding HIH. The encoded protein may also be "altered," and may contain deletions, insertions, or substitutions of amino acid residues which produce a silent change and result in a functionally equivalent HIH. Deliberate amino acid substitutions may be made on the basis of similarity in polarity, charge, solubility, hydrophobicity, hydrophilicity, and/or the amphipathic nature of the residues, as long as the biological or immunological activity of HIH is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments" refers to fragments of HIH which are preferably about 5 to about 15 amino acids in length and which retain some biological activity or immunological activity of HIH. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, for example, Dieffenbach, C. W. and G. S. Dveksler (1995) *PCR Primer, a Laboratory Manual*, Cold Spring Harbor Press, Plainview, N.Y.)

The term "antagonist," as it is used herein, refers to a molecule which, when bound to HIH, decreases the amount or the duration of the effect of the biological or immunological activity of HIH. Antagonists may include proteins, nucleic acids, carbohydrates, antibodies, or any other molecules which decrease the effect of HIH.

As used herein, the term "antibody" refers to intact molecules as well as to fragments thereof, such as Fab, F(ab')$_2$, and Fv fragments, which are capable of binding the epitopic determinant. Antibodies that bind HIH polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific DNA or RNA sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HIH, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation or an aqueous solution. Compositions comprising polynucleotide sequences encoding HIH or fragments of HIH may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW Fragment Assembly system (GCG, Madison, Wis.). Some sequences have been both extended and assembled to produce the consensus sequence .

As used herein, the term "correlates with expression of a polynucleotide" indicates that the detection of the presence of nucleic acids, the same or related to a nucleic acid sequence encoding HIH, by northern analysis is indicative of the presence of nucleic acids encoding HIH in a sample, and thereby correlates with expression of the transcript from the polynucleotide encoding HIH.

A "deletion," as the term is used herein, refers to a change in the amino acid or nucleotide sequence that results in the absence of one or more amino acid residues or nucleotides.

The term "derivative," as used herein, refers to the chemical modification of HIH, of a polynucleotide sequence encoding HIH, or of a polynucleotide sequence complementary to a polynucleotide sequence encoding HIH. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains a at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

"Human artificial chromosomes" (HACs), as described herein, are linear microchromosomes which may contain DNA sequences of about 10 Kb to 10 Mb in size, and which contain all of the elements required for stable mitotic chromosome segregation and maintenance. (Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

The term "microarray," as used herein, refers to an array of distinct polynucleotides or oligonucleotides arrayed on a substrate, such as paper, nylon or any other type of membrane, filter, chip, glass slide, or any other suitable solid support.

The term "modulate," as it appears herein, refers to a change in the activity of HIH. For example, modulation may cause an increase or a decrease in protein activity, binding characteristics, or any other biological, functional, or immunological properties of HIH.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimers," "primers," "oligomers," and "probes," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (Nielsen, P. E. et al. (1993) Anticancer Drug Des. 8:53–63.

The term "sample," as used herein, is used in its broadest sense. A biological sample suspected of containing nucleic acids encoding HIH, or fragments thereof, or HIH itself may comprise a bodily fluid; an extract from a cell, chromosome, organelle, or membrane isolated from a cell; a cell; genomic DNA, RNA, or cDNA (in solution or bound to a solid support); a tissue; a tissue print; and the like.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5× SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, and refers to cells which transiently express the inserted DNA or RNA for limited periods of time.

A "variant" of HIH, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of new human isomerase homologs (HIH), the polynucleotides encoding HIH, and the use of these compositions for the diagnosis, treatment, or prevention of cancer and immune disorders.

Nucleic acids encoding the HIH-I of the present invention were first identified in Incyte Clone 2255114 from the ovarian tumor cDNA library (OVARTUT01) using a computer search for amino acid sequence alignments. A consensus sequence, SEQ ID NO:2, was derived from the following overlapping and/or extended nucleic acid sequences: Incyte Clones 2255114 (OVARTUT01), 646760 (BRSTTUT02), 1854239 (HNT3AZT01), 1675040 9BLADNOT05), and 625499 (PGANNOT01).

In one embodiment, the invention encompasses a polypeptide comprising the amino acid sequence of SEQ ID NO:1, as shown in FIGS. 1A, 1B, 1C, 1D, 1E, 1F, and 1G. HIH-1 is 582 amino acids in length and contains an FKBP-type peptidyl-prolyl cis/trans isomerase signature sequence, comprising amino acids $L_{210}$ to $G_{238}$. HIH-1 also contains an endoplasmic reticulum targeting sequence consisting of residues $H_{579}$ through $L_{582}$, and an EF-hand calcium-binding domain consisting of residues $D_{555}$ through $L_{567}$. HIH-1 also has potential casein kinase II phosphorylation sites at residues $T_{72}$, $S_{81}$, $T_{100}$, $T_{184}$, $T_{189}$, $S_{296}$, $T_{301}$, $T_{391}$, $S_{409}$, $T_{418}$, $S_{484}$, $T_{546}$, $T_{563}$, and $S_{571}$, a potential cAMP/cGMP-dependent protein kinase phosphorylation site at residue $T_{342}$, a potential protein kinase C phosphorylation site at $T_{395}$, and a potential tyrosine kinase phosphorylation site at $Y_{83}$. In addition, HIH-1 has potential N-glycosylation sites at residues $N_{70}$, $N_{182}$, $N_{294}$, $N_{310}$, $N_{352}$, $N_{393}$, and $N_{407}$. As shown in FIGS. 4A, 4B, and 4C, HIH-1 has chemical and structural homology with mouse FKBP65 (GI 894162; SEQ ID NO:7). In particular, HIH-1 and FKBP65 share 88% identity. In addition, HIH-1 and FKBP65 share the isomerase signature sequence, the endoplasmic reticulum targeting sequence, and many of the potential phosphorylation sites. Northern analysis shows the expression of this sequence in various cells and tissues, at least 59% of which are immortalized or cancerous. Of particular note is the expression of HIH-1 in lymph nodes, inflamed colon, and synovium.

Nucleic acids encoding the HIH-2 of the present invention were first identified in Incyte Clone 292808 from the mononuclear cell cDNA library (TMLR3DT01) using a computer search for amino acid sequence alignments. A consensus sequence, SEQ ID NO:4, was derived from the following overlapping and/or extended nucleic acid sequences: Incyte Clones 292808 (TMLR3DT01), 387886 (THYMNOT02), 1444671 (THYRNOT03), 1430343 (SINTBST01) and 361577 (PROSNOT01).

In another embodiment, the invention encompasses a polypeptide comprising the amino acid sequence of SEQ ID NO:3, as shown in FIGS. 2A, 2B, 2C, and 2D. HIH-2 is 276 amino acids in length and contains a eukaryotic putative RNA-binding region signature sequence, comprising amino acids $R_{47}$ to $F_{54}$ HIH-2 has potential casein kinase II phosphorylation sites at residues $S_{97}$, and $T_{109}$, a potential cAMP/cGMP-dependent protein kinase phosphorylation site at residue $S_{106}$, potential protein kinase C phosphorylation sites at $T_3$, $T_4$, $T_{43}$, $T_{76}$, $S_{91}$, and $S_{106}$. In addition, HIH-2 has a potential N-glycosylation site at residues $N_{68}$. As shown in FIGS. 5A, and 5B, HIH-2 has chemical and structural homology with Schistosoma mansoni cyclophilin (SmCyP) (GI 894162; SEQ ID NO:8). In particular, HIH-2 and SmCyP share 41% identity. In addition, HIH-2 and SmCyP share the eukaryotic putative RNA-binding region signature sequence, the potential glycosylation site, and several potential phosphorylation sites. Northern analysis shows the expression of this sequence in various cells and tissues, at least 56% of which are immortalized or cancerous, and at least 30% of which are involved with inflammation. Of particular note is the expression of HIH-2 in lymphocytes, promonocytes and arthritic synovium.

Nucleic acids encoding the HIH-3 of the present invention were first identified in Incyte Clone 1419071 from the fetal kidney cDNA library (KIDNNOT09)) using a computer search for amino acid sequence alignments. A consensus sequence, SEQ ID NO:6, was derived from the following overlapping and/or extended nucleic acid sequences: Incyte Clones 1419071 (KIDNNOT09), 1459886 (COLNFET02), 1477963 (CORPNOT02), 1544045 (PROSTUT04), 234745 (SINTNOT02), and 938040 (CERVNOT01).

In another embodiment, the invention encompasses a polypeptide comprising the amino acid sequence of SEQ ID NO:5, as shown in FIGS. 3A, 3B, and 3C. HIH-3 is 249 amino acids in length and contains a leucine zipper pattern, comprising amino acids $L_5$ to $L_{26}$ HIH-3 has potential casein kinase II phosphorylation sites at residues $T_{38}$, $S_{127}$, and $S_{161}$, and a potential protein kinase C phosphorylation site at $S_{127}$. As shown in FIG. 6, HIH-3 has chemical and structural homology with *Methanococcus iannaschii* 2-hydroxyhepta-2,4-diene1,7-dioate isomerase (HHDDI) (GI 1500558; SEQ ID NO:9). In particular, HIH-3 and HHDDI share 41% identity. In addition, HIH-3 and HHDDI share a potential casein kinase phosphorylation site. Northern analysis shows the expression of this sequence in various cells and tissues, at least 55% of which are immortalized or cancerous, and at least 20% of which are involved with inflammation and tissues involved with the immune response. Of particular note is the expression of HIH-3 in reproductive tissue tumors including tumors of the prostate, cervix, uterus, breast and ovary.

The invention also encompasses HIH variants. A preferred HIH variant is one which has at least about 80%, more preferably at least about 90%, and most preferably at least about 95% amino acid sequence identity to the HIH amino acid sequence, and which contains at least one functional or structural characteristic of HIH.

The invention also encompasses polynucleotides which encode HIH. In a particular embodiment, the invention encompasses a polynucleotide sequence comprising the sequence of SEQ ID NO:2, which encodes an HIH-1, as shown in FIGS. 1A, 1B, 1C, 1D, 1E, 1F, and 1G. In a further embodiment, the invention encompasses a polynucleotide sequence comprising the sequence of SEQ ID NO:4, which encodes an HIH-2, as shown in FIGS. 2A, 2B, 2C, and 2D. In yet another embodiment, the invention encompasses a polynucleotide sequence comprising the sequence of SEQ ID NO:6, which encodes an HIH-3, as shown in FIGS. 3A, 3B, and 3C.

The invention also encompasses a variant of a polynucleotide sequence encoding HIH. In particular, such a variant polynucleotide sequence will have at least about 80%, more preferably at least about 90%, and most preferably at least about 95% polynucleotide sequence identity to the polynucleotide sequence encoding HIH. A particular aspect of the invention encompasses a variant of SEQ ID NO:2 which has at least about 80%, more preferably at least about 90%, and most preferably at least about 95% polynucleotide sequence identity to SEQ ID NO:2. The invention further encompasses a polynucleotide variant of SEQ ID NO:4 having at least about 80%, more preferably at least about 90%, and most preferably at least about 95% polynucleotide sequence identity to SEQ ID NO:4. The invention further encompasses a polynucleotide variant of SEQ ID NO:6 having at least about 80%, more preferably at least about 90%, and most preferably at least about 95% polynucleotide sequence identity to SEQ ID NO:4. Any one of the polynucleotide variants described above can encode an amino acid sequence which contains at least one functional or structural characteristic of HIH.

It will be appreciated by those skilled in the art that as a result of the degeneracy of the genetic code, a multitude of polynucleotide sequences encoding HIH, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HIH, and all such variations are to be considered as being specifically disclosed.

Although nucleotide sequences which encode HIH and its variants are preferably capable of hybridizing to the nucleotide sequence of the naturally occurring HIH under appropriately selected conditions of stringency, it may be advantageous to produce nucleotide sequences encoding HIH or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HIH and its derivatives without altering the encoded amino acid sequences include the production of RNA transcripts having more desirable properties, such as a greater half-life, than transcripts produced from the naturally occurring sequence.

The invention also encompasses production of DNA sequences which encode HIH and HIH derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HIH or any fragment thereof.

Also encompassed by the invention are polynucleotide sequences that are capable of hybridizing to the claimed polynucleotide sequences, and, in particular, to those shown in SEQ ID NO:2, SEQ ID NO:4, SEQ ID NO:6, a fragment of SEQ ID NO:2, a fragment of SEQ ID NO:4 or a fragment of SEQ ID NO:6, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing are well known and generally available in the art and may be used to practice any of the embodiments of the invention. The methods may employ such enzymes as the Klenow fragment of DNA polymerase I, SEQUENASE (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system (GIBCO/BRL, Gaithersburg, Md.). Preferably, the process is automated with machines such as the MICROLAB 2200 (Hamilton, Reno, Nev.), Peltier thermal cycler (PTC200; MJ Research, Watertown, Mass.), and the ABI CATALYST and 373 and 377 DNA sequencers (Perkin Elmer).

The nucleic acid sequences encoding HIH may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (Sarkar, G. (1993) PCR Methods Applic. 2:318–322.) In particular, genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (Triglia, T. et al. (1988) Nucleic Acids Res. 16:8186.) The primers may be designed using commercially available software such as OLIGO 4.06 primer analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HIH may be used in recombinant DNA molecules to direct expression of HIH, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HIH.

As will be understood by those of skill in the art, it may be advantageous to produce HIH-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HIH encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HIH may be ligated to a heterologous sequence to encode a fusion protein. For example, to screen peptide libraries for inhibitors of HIH activity, it may be useful to encode a chimeric HIH protein that can be recognized by a commercially available antibody. A fusion protein may also be engineered to contain a cleavage site located between the HIH encoding sequence and the heterologous protein sequence, so that HIH may be cleaved and purified away from the heterologous moiety.

In another embodiment, sequences encoding HIH may be synthesized, in whole or in part, using chemical methods well known in the art. (See Caruthers, M. H. et al. (1980) Nucl. Acids Res. Symp. Ser. 7: 215–223, and Horn, T. et al. (1980) Nucl. Acids Res. Symp. Ser. 7: 225–232.) Alternatively, the protein itself may be produced using chemical methods to synthesize the amino acid sequence of HIH, or a fragment thereof. For example, peptide synthesis can be performed using various solid-phase techniques (Roberge, J. Y. et al. (1995) Science 269:202–204) and automated synthesis may be achieved using the ABI 43 1A peptide synthesizer (Perkin Elmer).

The newly synthesized peptide may be substantially purified by preparative high performance liquid chromatography. (See, for example, Creighton, T. (1983) *Proteins Structures and Molecular Principles*, WH Freeman and Co., New York, N.Y.) The composition of the synthetic peptides may be confirmed by amino acid analysis or by sequencing. (See, for example, the Edman degradation procedure described in Creighton, supra.) Additionally, the amino acid sequence of HIH, or any part thereof, may be altered during direct synthesis and/or combined with sequences from other proteins, or any part thereof, to produce a variant polypeptide.

In order to express a biologically active HIH, the nucleotide sequences encoding HIH or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding HIH and appropriate transcriptional and translational control elements. These methods include in vitro recombinant DNA techniques, synthetic techniques, and in vivo genetic recombination. Such techniques are described in Sambrook, J. et al. (1989; *Molecular Cloning,*

*A Laboratory Manual*, Cold Spring Harbor Press, Plainview, N.Y.) and Ausubel, F. M. et al. (1989; *Current Protocols in Molecular Biology*, John Wiley & Sons, New York, N.Y.).

A variety of expression vector/host systems may be utilized to contain and express sequences encoding HIH. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions of the vector (i.e., enhancers, promoters, and 5' and 3' untranslated regions) which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, La Jolla, Calif.) or PSPORT1 plasmid (GIBCO/BRL), and the like, may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HIH, vectors based on SV40 or EBV may be used with an appropriate selectable marker.

In bacterial systems, a number of expression vectors may be selected depending upon the use intended for HIH. For example, when large quantities of HIH are needed for the induction of antibodies, vectors which direct high level expression of fusion proteins that are readily purified may be used. Such vectors include, but are not limited to, multifunctional *E. coli* cloning and expression vectors such as BLUESCRIPT (Stratagene), in which the sequence encoding HIH may be ligated into the vector in frame with sequences for the amino-terminal Met and the subsequent 7 residues of β-galactosidase so that a hybrid protein is produced, pIN vectors (Van Heeke, G. and S. M. Schuster (1989) J. Biol. Chem. 264:5503–5509), and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. For reviews, see Ausubel (supra) and Grant et al. (1987; Methods Enzymol. 153:516–544).

In cases where plant expression vectors are used, the expression of sequences encoding HIH may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, for example, Hobbs, S. or Murry, L. E. in *McGraw Hill Yearbook of Science and Technology* (1992) McGraw Hill, New York, N.Y.; pp. 191–196.)

An insect system may also be used to express HIH. For example, in one such system, *Autographa californica* nuclear polyhedrosis virus (AcNPV) is used as a vector to express foreign genes in *Spodoptera frugiperda* cells or in Trichoplusia larvae. The sequences encoding HIH may be cloned into a non-essential region of the virus, such as the polyhedrin gene, and placed under control of the polyhedrin promoter. Successful insertion of HIH will render the polyhedrin gene inactive and produce recombinant virus lacking coat protein. The recombinant viruses may then be used to infect, for example, *S. frugiperda* cells or Trichoplusia larvae in which HIH may be expressed. (Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding HIH may be ligated into an adenovirus transcription/translation complex consisting of the late promoter and tripartite leader sequence. Insertion in a non-essential E1 or E3 region of the viral genome may be used to obtain a viable virus which is capable of expressing HIH in infected host cells. (Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 M to 10 M are constructed and delivered via conventional delivery methods (liposomes, polycationic amino polymers, or vesicles) for therapeutic purposes.

Specific initiation signals may also be used to achieve more efficient translation of sequences encoding HIH. Such signals include the ATG initiation codon and adjacent sequences. In cases where sequences encoding HIH and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used, such as those described in the literature. (Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing HIH can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes (Wigler, M. et al. (1977) Cell 11:223–32) and adenine phosphoribosyl-transferase genes (Lowy, I. et al. (1980) Cell 22:817–23), which can be employed in tk$^-$ or apr$^-$ cells, respectively. Also, antimetabolite, antibiotic, or herbicide resistance can be used as the basis for selection. For example, dhfr confers resistance to methotrexate (Wigler, M. et al. (1980) Proc. Natl. Acad. Sci. 77:3567–70); npt confers resistance to the aminoglycosides neomycin and G-418 (Colbere-Garapin, F. et al (1981) J. Mol. Biol. 150:1–14); and als or pat confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine. (Hartman, S. C. and R. C. Mulligan (1988) Proc. Natl. Acad. Sci. 85:8047–51.) Recently, the use of visible markers has gained popularity with such markers as anthocyanins, β glucuronidase and its substrate GUS, and luciferase and its substrate luciferin. These markers can be used not only to identify transformants, but also to quantify the amount of transient or stable protein expression attributable to a specific vector system. (Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HIH is inserted within a marker gene sequence, transformed cells containing sequences encoding HIH can be identified by the absence of marker gene function. Alternatively, a marker gene can be placed in tandem with a sequence encoding HIH under the control of a single promoter. Expression of the marker gene in response to induction or selection usually indicates expression of the tandem gene as well.

Alternatively, host cells which contain the nucleic acid sequence encoding HIH and express HIH may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding HIH can be detected by DNA-DNA or DNA-RNA hybridization or amplification using probes or fragments or fragments of polynucleotides encoding HIH. Nucleic acid amplification based assays involve the use of oligonucleotides or oligomers based on the sequences encoding HIH to detect transformants containing DNA or RNA encoding HIH.

A variety of protocols for detecting and measuring the expression of HIH, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HIH is preferred, but a competitive binding assay may be employed. These and other assays are well described in the art, for example, in Hampton, R. et al. (1990; *Serological Methods, a Laboratory Manual*, APS Press, St Paul, Minn.) and in Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HIH include oligolabeling, nick translation, end-labeling, or PCR amplification using a labeled nucleotide. Alternatively, the sequences encoding HIH, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HIH may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HIH may be designed to contain signal sequences which direct secretion of HIH through a prokaryotic or eukaryotic cell membrane. Other constructions may be used to join sequences encoding HIH to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the HIH encoding sequence may be used to facilitate purification. One such expression vector provides for expression of a fusion protein containing HIH and a nucleic acid encoding 6 histidine residues preceding a thioredoxin or an enterokinase cleavage site. The histidine residues facilitate purification on immobilized metal ion affinity chromatography (IMAC; described in Porath, J. et al. (1992) Prot. Exp. Purif. 3: 263–281), while the enterokinase cleavage site provides a means for purifying HIH from the fusion protein. A discussion of vectors which contain fusion proteins is provided in Kroll, D. J. et al. (1993; DNA Cell Biol. 12:441–453).

Fragments of HIH may be produced not only by recombinant production, but also by direct peptide synthesis using solid-phase techniques. (Merrifield J. (1963) J. Am. Chem. Soc. 85:2149–2154.) Protein synthesis may be performed by manual techniques or by automation. Automated synthesis may be achieved, for example, using the Applied Biosystems 431 A peptide synthesizer (Perkin Elmer). Various fragments of HIH may be synthesized separately and then combined to produce the full length molecule.

Therapeutics

Chemical and structural homology exists between HIH-1 and FKBP65 from mouse (GI 894162). In addition, HIH-1 is expressed in cancerous tissues, lymph nodes, inflamed colon, and synovium. Therefore, HIH-1 appears to play a role in cancer and immune disorders.

Chemical and structural homology exists between HIH-2 and SmCyP from *Schistosoma mansoni* (GI 2190553). In addition, HIH-2 is expressed in cancerous tissues, in lymphocytes, promonocytes and arthritic synovium. Therefore, HIH-2 appears to play a role in cancer and immune disorders.

Chemical and structural homology exists between HIH-3 and HHDDI from *Methanococcus jannaschii* (GI 1500558). In addition, HIH-3 is expressed in cancerous tissues, and in tissues involved in the inflammatory response. Therefore, HIH-3 appears to play a role in cancer and immune disorders.

Therefore, in one embodiment, an antagonist of HIH may be administered to a subject to treat or prevent a cancer. Such a cancer may include, but is not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HIH may be used directly as an antagonist or indirectly as a targeting or delivery mechanism for bringing a pharmaceutical agent to cells or tissue which express HIH.

In an additional embodiment, a vector expressing the complement of the polynucleotide encoding HIH may be administered to a subject to treat or prevent a cancer including, but not limited to, those described above.

In a further embodiment, an antagonist of HIH may be administered to a subject to treat or prevent an immune disorder including, but not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. In one aspect, an antibody which specifically binds HIH may be used directly as an antagonist or indirectly as a targeting or delivery mechanism for bringing a pharmaceutical agent to cells or tissue which express HIH.

In an additional embodiment, a vector expressing the complement of the polynucleotide encoding HIH may be administered to a subject to treat or prevent an immune disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HIH may be produced using methods which are generally known in the art. In particular, purified HIH may be used to produce antibodies or to screen libraries of pharmaceutical agents to identify those which specifically bind HIH. Antibodies to HIH may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HIH or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HIH have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HIH amino acids may be fused with those of another protein, such as KLH, and antibodies to the chimeric molecule may be produced.

Monoclonal antibodies to HIH may be prepared using any technique which provides for the production of antibody molecules by continuous cell lines in culture. These include, but are not limited to, the hybridoma technique, the human B-cell hybridoma technique, and the EBV-hybridoma technique. (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HIH-specific single chain antibodies. Antibodies with related specificity, but of distinct idiotypic composition, may be generated by chain shuffling from random combinatorial immunoglobulin libraries. (Burton D. R. (1991) Proc. Natl. Acad. Sci. 88:11120–11123.)

Antibodies may also be produced by inducing in vivo production in the lymphocyte population or by screening immunoglobulin libraries or panels of highly specific binding reagents as disclosed in the literature. (Orlandi, R. et al. (1989) Proc. Natl. Acad. Sci. 86: 3833–3837, and Winter, G. et al. (1991) Nature 349:293–299.)

Antibody fragments which contain specific binding sites for HIH may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (Huse, W. D. et al. (1989) Science 254:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HIH and its specific antibody. A two-site, monoclonal-based immunoassay utilizing monoclonal antibodies reactive to two non-interfering HIH epitopes is preferred, but a competitive binding assay may also be employed. (Maddox, supra.)

In another embodiment of the invention, the polynucleotides encoding HIH, or any fragment or complement thereof, may be used for therapeutic purposes. In one aspect, the complement of the polynucleotide encoding HIH may be used in situations in which it would be desirable to block the transcription of the mRNA. In particular, cells may be transformed with sequences complementary to polynucleotides encoding HIH. Thus, complementary molecules or fragments may be used to modulate HIH activity, or to achieve regulation of gene function. Such technology is now well known in the art, and sense or antisense oligonucleotides or larger fragments can be designed from various locations along the coding or control regions of sequences encoding HIH.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequence complementary to the polynucleotides of the gene encoding HIH. These techniques are described, for example, in Sambrook (supra) and in Ausubel (supra).

Genes encoding HIH can be turned off by transforming a cell or tissue with expression vectors which express high levels of a polynucleotide or fragment thereof encoding HIH. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HIH. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (Gee, J. E. et al. (1994) in Huber, B. E. and B. I. Carr, *Molecular and Immunologic Approaches*, Futura Publishing Co., Mt. Kisco, N.Y.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules specifically and efficiently catalyze endonucleolytic cleavage of sequences encoding HIH.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HIH. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art, such as those described in Goldman, C. K. et al. (1997; Nature Biotechnology 15:462–466).

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HIH, antibodies to HIH, and mimetics, agonists, antagonists, or inhibitors of HIH. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HIH, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays of neoplastic cells, for example, or in animal models, usually mice, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HIH or fragments thereof, antibodies of HIH, and agonists, antagonists or inhibitors of HIH, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of toxic to therapeutic effects is the therapeutic index, which can be expressed as the LD50/ED50 ratio. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on the half-life and clearance rate of the particular formulation.

Normal dosage amounts may vary from 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HIH may be used for the diagnosis of disorders characterized by expression of HIH-1, or in assays to monitor patients being treated with HIH or agonists, antagonists, and inhibitors of HIH. Antibodies useful for diagnostic purposes may be prepared in the same manner as those described above for therapeutics. Diagnostic assays for HIH include methods which utilize the antibody and a label to detect HIH in human body fluids or in extracts of cells or tissues. The antibodies may be used with or without modification, and may be labeled by covalent or non-covalent joining with a reporter molecule. A wide variety of reporter molecules, several of which are described above, are known in the art and may be used.

A variety of protocols for measuring HIH, including ELISAs, RIAs, and FACS, are known in the art and provide a basis for diagnosing altered or abnormal levels of HIH expression. Normal or standard values for HIH expression are established by combining body fluids or cell extracts taken from normal mammalian subjects, preferably human, with antibody to HIH under conditions suitable for complex formation The amount of standard complex formation may be quantified by various methods, preferably by photometric means. Quantities of HIH expressed in subject, control, and disease samples from biopsied tissues are compared with the standard values. Deviation between standard and subject values establishes the parameters for diagnosing disease.

In another embodiment of the invention, the polynucleotides encoding HIH may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HIH may be correlated with disease. The diagnostic assay may be used to distinguish between absence, presence, and excess expression of HIH, and to monitor regulation of HIH levels during therapeutic intervention.

In one aspect, hybridization with PCR probes which are capable of detecting polynucleotide sequences, including genomic sequences, encoding HIH or closely related molecules may be used to identify nucleic acid sequences which encode HIH. The specificity of the probe, whether it is made from a highly specific region (e.g., the 5' regulatory region) or from a less specific region (e.g., the 3' coding region), and the stringency of the hybridization or amplification (maximal, high, intermediate, or low), will determine whether the probe identifies only naturally occurring sequences encoding HIH, alleles, or related sequences.

Probes may also be used for the detection of related sequences, and should preferably contain at least 50% of the nucleotides from any of the HIH encoding sequences. The hybridization probes of the subject invention may be DNA or RNA and may be derived from the sequences of SEQ ID NO:2, SEQ ID NO:4, SEQ ID NO:6, or from genomic sequences including promoter and enhancer elements and introns of the naturally occurring HIH.

Means for producing specific hybridization probes for DNAs encoding HIH include the cloning of polynucleotide sequences encoding HIH or HIH derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or $^{35}$S, or by enzymatic labels, such as alkaline phosphatase coupled to the probe via avidin/biotin coupling systems, and the like.

Polynucleotide sequences encoding HIH may be used for the diagnosis of a disorder associated with expression of HIH. Examples of such a disorder include, but are not limited to, cancers, such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immune disorders, such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis. hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. The polynucleotide sequences encoding HIH may be used in Southern or northern analysis, dot blot, or other membrane-based technologies; in PCR technologies; in dipstick, pin, and ELISA assays; and in microarrays utilizing fluids or tissues from patient biopsies to detect altered HIH expression. Such qualitative or quantitative methods are well known in the art.

In a particular aspect, the nucleotide sequences encoding HIH may be useful in assays that detect the presence of associated disorders, particularly those mentioned above. The nucleotide sequences encoding HIH may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered from that of a comparable control sample, the nucleotide sequences have hybridized with nucleotide sequences in the sample, and the presence of altered levels of nucleotide sequences encoding HIH in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis of a disorder associated with expression of HIH, a normal or standard profile for expression is established. This may be accomplished by combining body fluids or cell extracts taken from normal subjects, either animal or human, with a sequence, or a fragment thereof, encoding HIH, under conditions suitable for hybridization or amplification. Standard hybridization may be quantified by comparing the values obtained from normal subjects with values from an experiment in which a known amount of a substantially purified polynucleotide is used. Standard values obtained from normal samples may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to evaluate whether the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HIH may involve the use of PCR. These oligomers may be chemically synthesized, generated enzymatically, or produced in vitro. Oligomers will preferably contain a fragment of a polynucleotide encoding HIH, or a fragment of a polynucleotide complementary to the polynucleotide encoding HIH, and will be employed under optimized conditions for identification of a specific gene or condition. Oligomers may also be employed under less stringent conditions for detection or quantitation of closely related DNA or RNA sequences.

Methods which may also be used to quantitate the expression of HIH include radiolabeling or biotinylating nucleotides, coamplification of a control nucleic acid, and interpolating results from standard curves. (Melby, P. C. et al. (1993) J. Immunol. Methods 159:235–244, and Duplaa, C. et al. (1993) Anal. Biochem. 212: 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously (to produce a transcript image) and to identify genetic variants, mutations, and polymorphisms. This information may be used in determining gene function, in understanding the genetic basis of a disorder, in diagnosing a disorder, and in developing and monitoring the activities of therapeutic agents.

In one embodiment, the microarray is prepared and used according to methods known in the art, such as those described in published PCT application WO95/11995 (Chee et al.), Lockhart, D. J. et al. (1 996; Nat. Biotech. 14:1675–1680), and Schena, M. et al. (1996; Proc. Natl. Acad. Sci. 93:10614–10619).

The microarray is preferably composed of a large number of unique single-stranded nucleic acid sequences, usually either synthetic antisense oligonucleotides or fragments of cDNAs, fixed to a solid support. The oligonucleotides are preferably about 6 to 60 nucleotides in length, more preferably about 15 to 30 nucleotides in length, and most preferably about 20 to 25 nucleotides in length. For a certain type of microarray, it may be preferable to use oligonucleotides which are about 7 to 10 nucleotides in length. The microarray may contain oligonucleotides which cover the known 5' or 3' sequence, or may contain sequential oligonucleotides which cover the full length sequence or unique oligonucleotides selected from particular areas along the length of the sequence. Polynucleotides used in the microarray may be oligonucleotides specific to a gene or genes of interest in which at least a fragment of the sequence is known or oligonucleotides specific to one or more unidentified cDNAs common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from about 2 to 1,000,000.

In order to produce oligonucleotides to a known sequence for a microarray, the gene of interest is examined using a computer algorithm which starts at the 5' end, or, more preferably, at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon, any other type of membrane, filter, chip, glass slide, or any other suitable solid support.

In one aspect, the oligonucleotides may be synthesized on the surface of the substrate by using a chemical coupling procedure and an ink jet application apparatus, such as that described in published PCT application WO95/251 116 (Baldeschweiler et al.). In another aspect, a grid array analogous to a dot or slot blot (HYBRIDOT apparatus, GIBCO/BRL) may be used to arrange and link cDNA fragments or oligonucleotides to the surface of a substrate using a vacuum system or thermal, UV, mechanical or chemical bonding procedures. In yet another aspect, an array may be produced by hand or by using available devices, materials, and machines (including Brinkmann) multichannel pipettors or robotic instruments), and may contain 8, 24, 96, 384, 1536, or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and OLIGOLABELING or TRANSPROBE kits (Pharmacia & Upjohn) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine the degree of complementarity and the relative abundance of each oligonucleotide sequence on the microarray. A detection system may be used to measure the absence, presence, and amount of hybridization for all of the distinct sequences simultaneously. This data may be used for large scale correlation studies or for functional analysis of the sequences, mutations, variants, or polymorphisms among samples. (Heller, R. A. et al. (1997) Proc. Natl. Acad. Sci. 94:2150–2155.)

In another embodiment of the invention, nucleic acid sequences encoding HIH may be used to generate hybridization probes useful for mapping the naturally occurring genomic sequence. The sequences may be mapped to a particular chromosome, to a specific region of a chromosome, or to artificial chromosome constructions, such as human artificial chromosomes (HACs), yeast artificial chromosomes (YACs), bacterial artificial chromosomes (BACs), bacterial P1 constructions, or single chromosome cDNA libraries, such as those reviewed in Price, C. M. (1993; Blood Rev. 7:127–134) and Trask, B. J. (1991; Trends Genet. 7:149–154).

Fluorescent in situ hybridization (FISH, as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at the Online Mendelian Inheritance in Man (OMIM) site. Correlation between the location of the gene encoding HIH on a physical chromosomal map and a specific disorder, or predisposition to a specific disorder, may help define the region of DNA associated with that disorder. The nucleotide sequences of the subject invention may be used to detect differences in gene sequences between normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc., among normal, carrier, or affected individuals.

In another embodiment of the invention, HIH, its catalytic or immunogenic fragments, or oligopeptides thereof can be used for screening libraries of compounds in any of a variety t5 of drug screening techniques. The fragment employed in such screening may be free in solution, affixed to a solid support, borne on a cell surface, or located intracellularly. The formation of binding complexes between HIH and the agent being tested may be measured.

Another technique for drug screening which may be used provides for high throughput screening of compounds having suitable binding affinity to the protein of interest as described in published PCT application WO84/03564. In this method, large numbers of different small test compounds are synthesized on a solid substrate, such as plastic pins or some other surface. The test compounds are reacted with HIH, or fragments thereof, and washed. Bound HIH is then detected by methods well known in the art. Purified HIH can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HIH specifically compete with a test compound for binding HIH. In this manner, antibodies can be used to detect the presence of any peptide which shares one or more antigenic determinants with HIH.

In additional embodiments, the nucleotide sequences which encode HIH may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. cDNA Library Construction

OVARTUT01

The OVARTUT01 cDNA library was constructed from tumorous ovary tissue obtained from a 43 year old Caucasian female with a malignant neoplasm. The patient history indicated a previous normal delivery and a vaginal hysterectomy. Also reported in the patient history were previous diagnoses of hepatitis, cerebrovascular disease, atherosclerosis and mitral valve disorder; however, the patient was not taking medication for any of these conditions at the time of surgery.

The frozen tissue was homogenized and lysed using a POLYTRON PT-3000 homogenizer (Brinkmann Instruments, Westbury, N.J.) in guanidinium isothiocyanate solution. The lysate was centrifuged over a 5.7 M CsCl cushion using an SW28 rotor in a L8-70M ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. RNA extraction and precipitation were repeated as before. The mRNA was then isolated with the OLIGOTEX kit (QIAGEN, Inc. Chatsworth, Calif.) and used to construct the cDNAs. The cDNAs were ligated into pSport I.

TMLR3DT01

The TMLR3DT01 cDNA library was constructed from normal peripheral blood T-lymphocytes obtained from two unrelated Caucasian males aged 25 and 29 years. This library represents a mixture of allogeneically stimulated human T cell populations obtained from Ficoll/Hypaque purified buffy coats. The cells from the two different donors (not typed for HLA alleles) were incubated at a density of $1 \times 10^6$/ml, cultured for 96 hours in DME containing 10% human serum, washed in PBS, scraped and lysed immediately in buffer containing guanidinium isothiocyanate. The lysate was extracted twice with a mixture of phenol and chloroform, pH 8.0 and centrifuged over a CsCl cushion using an SW28 rotor in an L8-70M ultracentrifuge (Beckman Instruments). The RNA was precipitated using 0.3 M sodium acetate and 2.5 volumes of ethanol, resuspended in water and DNase treated for 15 min at 37° C. The total RNA was isolated using the OLIGOTEX kit (QIAGEN), and used to make cDNAs. The cDNAs were ligated into Lambda UNIZAP vector.

KIDNNOT09

The KIDNNOT09 cDNA library was constructed using the kidney tissue of a Caucasian male fetus, who died at 23 weeks' gestation from premature birth. Serology was negative. Family history included diabetes in the mother.

The frozen tissue was homogenized and lysed using a POLYTRON PT-3000 homogenizer (Brinkmann Instruments, Westbury, N.J.) in guanidinium isothiocyanate solution. The lysate was centrifuged over a 5.7 M CsCl cushion using an SW28 rotor in an L8-70M ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. RNA extraction and precipitation were repeated as before. The mRNA was then isolated with the OLIGOTEX kit (QIAGEN) and used to make cDNAs. The cDNAs were ligated into the pINCY vector.

OVARTUT01, TMLR3DT01 and KIDNNOT09

The mRNA was handled according to the recommended protocols in the SUPERSCRIPT plasmid system (Cat. #18248-013; Gibco/BRL). cDNAs were fractionated on a SEPHAROSE CL4B column (Cat. #275105-01; Pharmacia), and those cDNAs exceeding 400 bp were ligated into the described vectors and subsequently transformed into DH5α competent cells (Cat. #18258-012; Gibco/BRL).

II. Isolation and Sequencing of cDNA Clones

Plasmid DNA was released from the cells and purified using the R.E.A.L. PREP 96 plasmid kit (Catalog #26173; QIAGEN).The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94: 441f), using a MICROLAB 2200 (Hamilton, Reno, Nev.) in combination with Peltier thermal cyclers (PTC200 from MJ Research, Watertown, Mass.) and Applied Biosystems 377 DNA sequencing systems.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992; Protein Engineering 5:35–51), could have been used when dealing with primary sequence patterns and secondary structure gap penalties. The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-10}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (Sambrook, supra).

Analogous computer techniques applying BLAST are used to search for identical or related molecules in nucleotide databases such as GenBank or the LIFESEQ™ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HIH occurs. Abundance and percent abundance are also reported. Abundance directly reflects the number of times a particular transcript is represented in a cDNA library, and percent abundance is abundance divided by the total number of sequences examined in the cDNA library.

V. Extension of HIH Encoding Polynucleotides

The nucleic acid sequences of Incyte Clones 2255114, 292808, and 1419071 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier thermal cycler (PTC200; M. J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent *E. coli* cells (in 40 µl of appropriate media) were transformed with 3 µl of ligation mixture and cultured in 80 µl of SOC medium. (Sambrook, supra). After incubation for one hour at 37° C., the *E. coli* mixture was plated on Luria Bertani (LB) agar (Sambrook, supra) containing 2× Carb. The following day, several colonies were randomly picked from each plate and cultured in 150 µl of liquid LB/2× Carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:2, SEQ ID NO:4, and SEQ ID NO:6 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2, SEQ ID NO:4, and SEQ ID NO:6 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software National Biosciences) and labeled by combining 50 pmol of each oligomer and 250 µCi of [γ-$^{32}$ P] adenosine triphosphate (Amersham) and T4 polynucleotide kinase (DuPont NEN, Boston, Mass.). The labeled oligonucleotides are substantially purified using a Sephadex G-25 superfine resin column (Pharmacia & Upjohn). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba 1, or Pvu II (DuPont NEN®).

The DNA fro m each digest is fractionated on a 0.7 percent agarose gel and transferred to nylon membranes NYTRAN Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots or the blots are placed in a PHOSPHOIMAGER cassette (Molecular Dynamics, Sunnyvale, Calif.) for several hours, hybridization patterns ar e compared visually.

VII. Microarrays

To produce oligonucleotides for a microarray, one of the nucleotide sequences of the present invention is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). A matched set of oligonucleotides are created in which one nucleotide in the center of each sequence is altered. This process is repeated for each gene in the microarray, and double sets of twenty 20-mers are synthesized and arranged on the surface of the silicon chip using a light-directed chemical process, such as that described in Chee (supra).

In the alternative, a chemical coupling procedure and an ink jet device are used to synthesize oligomers on the surface of a substrate. (See Baldeschweiler, supra.) In another alternative, a grid array analogous to a dot or slot blot is used to arrange and link cDNA fragments or oligonucleotides to the surface of a substrate using a vacuum system or thermal, UV, mechanical, or chemical bonding procedures. A typical array may be produced by hand or using available materials and machines and contain grids of 8 dots, 24 dots, 96 dots, 384 dots, 1536 dots, or 6144 dots. After hybridization, the microarray is washed to remove nonhybridized probes, and a scanner is used to determine the levels and patterns of fluorescence. The scanned image is examined to determine the degree of complementarity and the relative abundance/expression level of each oligonucleotide sequence in the microarray.

VIII. Complementary Polynucleotides

Sequences complementary to the HIH-encoding sequences, or any parts thereof, are used to detect, decrease, or inhibit expression of naturally occurring HIH. Although use of oligonucleotides comprising from about 15 to 30 base pairs is described, essentially the same procedure is used with smaller or with larger sequence fragments. Appropriate oligonucleotides are designed using OLIGO 4.06 software and the coding sequence of HIH. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HIH-encoding transcript.

IX. Expression of HIH

Expression of HIH is accomplished by subcloning the cDNAs into appropriate vectors and transforming the vectors into host cells. In this case, the cloning vector is also used to express HIH in *E. coli*. This vector contains a promoter for β-galactosidase upstream of the cloning site, followed by sequence containing the amino-terminal Met and the subsequent seven residues of β-galactosidase. Immediately following these eight residues is a bacteriophage promoter useful for transcription and a linker containing a number of unique restriction sites.

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of HIH into bacterial growth media which can be used directly in the following assay for activity.

X. Demonstration of HIH Activity

HIH-2 and HIH-2

Peptidyl prolyl cis/trans isomerase activity can be assayed by an enzyme assay described by Rahfeld, J. U., et al. (1994) (FEBS Lett. 352: 180–184). The assay is performed at 10° C. in 35 mM HEPES buffer, pH 7.8, containing chymotrypsin (0.5 mg/ml) and HIH at a variety of concentrations. Under these assay conditions, the substrate, Suc-Ala-Xaa-Pro-Phe-4-NA, is in equilibrium with respect to the prolyl bond, with 80–95% in trans and 5–20% in cis conformation. An aliquot (2 ul) of the substrate dissolved in dimethyl sulfoxide (10 mg/ml) is added to the reaction mixture described above. Only the cis isomer of the substrate is a substrate for cleavage by chymotrypsin. Thus, as the substrate is isomerized by HIH, the product is cleaved by chymotrypsin to produce 4-nitroanilide, which is detected by it's absorbance at 390 nm. 4-Nitroanilide appears in a time-dependent and an HIH-1 or HIH-2 concentration-dependent manner.

HIH-3

The activity of HIH-3 can be determined by measuring the isomerization of 2hydroxyhepta-2,4-diene-1,7-dioate to2-oxo-hept-3-ene-1,7-dioate. The reaction mixture consists of 0.1 M sodium phosphate buffer, pH 7.5, 2-hydroxyhepta-2,4-diene-1,7-dioate, 0.05 umol, and varying amounts of HIH-3, which is added last. 2-Hydroxyhepta-2,4-diene-1,7-dioate absorbs at 276 nm. Thus, as this substrate is consumed, the absorbance at 276 nm decreases, in a time-dependent and HIH-3 concentration-dependent manner (Jenkins, J. R., and Cooper, R. A. (1988) J. Bacteriol. 170: 5317–5324).

XI. Production of HIH Specific Antibodies

HIH substantially purified using PAGE electrophoresis (Sambrook, supra), or other purification techniques, is used to immunize rabbits and to produce antibodies using standard protocols. The HIH amino acid sequence is analyzed using DNASTAR software (DNASTAR Inc) to determine regions of high immunogenicity, and a corresponding oligopeptide is synthesized and used to raise antibodies by means known to those of skill in the art. Selection of appropriate epitopes, such as those near the C-terminus or in hydrophilic regions, is described by Ausubel (supra) and by others.

Typically, the oligopeptides are 15 residues in length, and are synthesized using an Applied Biosystems 431A peptide synthesizer using fmoc-chemistry and coupled to KLH (Sigma, St. Louis, Mo.) by reaction with N-maleimidobenzoyl-N-hydroxysuccinimide ester (MBS), following the procedure described in Ausubel et al., supra. Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radioiodinated goat anti-rabbit IgG.

XII. Purification of Naturally Occurring HIH Using Specific Antibodies

Naturally occurring or recombinant HIH is substantially purified by immunoaffinity chromatography using antibodies specific for HIH. An immunoaffinity column is constructed by covalently coupling HIH antibody to an activated chromatographic resin, such as CNBr-activated SEPHAROSE (Pharmacia & Upjohn). After the coupling, the resin is blocked and washed according to the manufacturer's instructions.

Media containing HIH are passed over the immunoaffinity column, and the column is washed under conditions that allow the preferential absorbance of HIH (e.g., high ionic strength buffers in the presence of detergent). The column is eluted under conditions that disrupt antibody/HIH binding (e.g., a buffer of pH 2 to pH 3, or a high concentration of a chaotrope, such as urea or thiocyanate ion), and HIH is collected.

XIII. Identification of Molecules Which Interact with HIH

HIH or biologically active fragments thereof are labeled with $^{125}I$ Bolton-Hunter reagent. (Bolton et al. (1973) Biochem. J. 133:529.) Candidate molecules previously arrayed in the wells of a multi-well plate are incubated with the labeled HIH, washed, and any wells with labeled HIH complex are assayed. Data obtained using different concentrations of HIH are used to calculate values for the number, affinity, and association of HIH with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a polypeptide comprising the amino acid sequence of SEQ ID NO:1.

2. A composition comprising the polynucleotide sequence of claim 1.

3. An isolated and purified polynucleotide sequence which is completely complementary to the polynucleotide sequence of claim 1.

4. An isolated and purified polynucleotide sequence consisting of SEQ ID NO:2.

5. An isolated and purified polynucleotide sequence which is completely complementary to the polynucleotide sequence of claim 4.

6. An expression vector comprising the polynucleotide sequence of claim 1.

7. A host cell comprising the expression vector of claim 6.

8. A method for producing a polypeptide comprising the amino acid sequence of SEQ ID NO:1, the method comprising the steps of:

a) culturing the host cell of claim 7 under conditions suitable for the expression of the polypeptide; and b) recovering the polypeptide from the host cell culture.

9. A method for detecting a polynucleotide encoding a polypeptide comprising SEQ ID NO:1 in a biological sample containing nucleic acids, the method comprising the steps of:

(a) hybridizing the polynucleotide of claim 3 to at least one of the nucleic acids in the biological sample, thereby forming a hybridization complex; and (b) detecting the hybridization complex, wherein the presence of the hybridization complex correlates with the presence of the polynucleotide encoding the polypeptide in the biological sample.

10. The method of claim 9 wherein the nucleic acids of the biological sample are amplified by the polymerase chain reaction prior to hybridization. the polypeptide in the biological sample.

* * * * *

UNITED STATES PATENT AND TRADEMARK OFFICE
CERTIFICATE OF CORRECTION

| | |
|---|---|
| PATENT NO. | : 5,989,860 |
| DATED | : November 23, 1999 |
| INVENTOR(S) | : Olga Bandman, Jennifer L. Hillman, Karl J. Guegler, Neil C. Corley and Purvi Shah |

It is certified that error appears in the above-identified patent and that said Letters Patent is hereby corrected as shown below:

<u>Column 56,</u>
Lines 51 and 52, delete "the polypeptide in the biological sample."

Signed and Sealed this

Twenty-sixth Day of November, 2002

*Attest:*

JAMES E. ROGAN
*Attesting Officer*     *Director of the United States Patent and Trademark Office*

SEQUENCE LISTING

```
(1) GENERAL INFORMATION:

(iii) NUMBER OF SEQUENCES: 9

(2) INFORMATION FOR SEQ ID NO:1:

(i) SEQUENCE CHARACTERISTICS:
          (A) LENGTH: 582 amino acids
          (B) TYPE: amino acid
          (C) STRANDEDNESS: single
          (D) TOPOLOGY: linear (vii) IMMEDIATE SOURCE:
          (A) LIBRARY: OVARTUT01
          (B) CLONE: 2255114

(xi) SEQUENCE DESCRIPTION: SEQ ID NO:1:

Met Phe Pro Ala Gly Pro Pro Ser His Ser Leu Leu Arg Leu Pro Leu
 1               5                  10                  15

Leu Gln Leu Leu Leu Leu Val Val Gln Ala Val Gly Arg Gly Leu Gly
            20                  25                  30

Arg Ala Ser Pro Ala Gly Gly Pro Leu Glu Asp Val Val Ile Glu Arg
        35                  40                  45

Tyr His Ile Pro Arg Ala Cys Pro Arg Glu Val Gln Met Gly Asp Phe
    50                  55                  60

Val Arg Tyr His Tyr Asn Gly Thr Phe Glu Asp Gly Lys Lys Phe Asp
65                  70                  75                  80

Ser Ser Tyr Asp Arg Asn Thr Leu Val Ala Ile Val Val Gly Val Gly
                85                  90                  95

Arg Leu Ile Thr Gly Met Asp Arg Gly Leu Met Gly Met Cys Val Asn
            100                 105                 110

Glu Arg Arg Arg Leu Ile Val Pro Pro His Leu Gly Tyr Gly Ser Ile
        115                 120                 125
```

-continued

```
Gly Leu Ala Gly Leu Ile Pro Pro Asp Ala Thr Leu Tyr Phe Asp Val
    130                 135                 140

Val Leu Leu Asp Val Trp Asn Lys Glu Asp Thr Val Gln Val Ser Thr
145                 150                 155                 160

Leu Leu Arg Pro Pro His Cys Pro Arg Met Val Gln Asp Gly Asp Phe
                165                 170                 175

Val Arg Tyr His Tyr Asn Gly Thr Leu Leu Asp Gly Thr Ser Phe Asp
            180                 185                 190

Thr Ser Tyr Ser Lys Gly Gly Thr Tyr Asp Thr Tyr Val Gly Ser Gly
        195                 200                 205

Trp Leu Ile Lys Gly Met Asp Gln Gly Leu Leu Gly Met Cys Pro Gly
        210                 215                 220

Glu Arg Arg Lys Ile Ile Ile Pro Pro Phe Leu Ala Tyr Gly Glu Lys
225                 230                 235                 240

Gly Tyr Gly Thr Val Ile Pro Pro Gln Ala Ser Leu Val Phe His Val
                245                 250                 255

Leu Leu Ile Asp Val His Asn Pro Lys Asp Ala Val Gln Leu Glu Thr
                260                 265                 270

Leu Glu Leu Pro Pro Gly Cys Val Arg Arg Ala Gly Ala Gly Asp Phe
        275                 280                 285

Met Arg Tyr His Tyr Asn Gly Ser Leu Met Asp Gly Thr Leu Phe Asp
    290                 295                 300

Ser Ser Tyr Ser Arg Asn His Thr Tyr Asn Thr Tyr Ile Gly Gln Gly
305                 310                 315                 320

Tyr Ile Ile Pro Gly Met Asp Gln Gly Leu Gln Gly Ala Cys Met Gly
                325                 330                 335

Glu Arg Arg Arg Ile Thr Ile Pro Pro His Leu Ala Tyr Gly Glu Asn
            340                 345                 350

Gly Thr Gly Asp Lys Ile Pro Gly Ser Ala Val Leu Ile Phe Asn Val
        355                 360                 365

His Val Ile Asp Phe His Asn Pro Ala Asp Val Val Glu Ile Arg Thr
    370                 375                 380

Leu Ser Arg Pro Ser Glu Thr Cys Asn Glu Thr Thr Lys Leu Gly Asp
385                 390                 395                 400

Phe Val Arg Tyr His Tyr Asn Cys Ser Leu Leu Asp Gly Thr Gln Leu
                405                 410                 415

Phe Thr Ser His Asp Tyr Gly Ala Pro Gln Glu Ala Thr Leu Gly Ala
            420                 425                 430

Asn Lys Val Ile Glu Gly Leu Asp Thr Gly Leu Gln Gly Met Cys Val
        435                 440                 445

Gly Glu Arg Arg Gln Leu Ile Val Pro Pro His Leu Ala His Gly Glu
    450                 455                 460

Ser Gly Ala Arg Gly Val Pro Gly Ser Ala Val Leu Leu Phe Glu Val
465                 470                 475                 480

Glu Leu Val Ser Arg Glu Asp Gly Leu Pro Thr Gly Tyr Leu Phe Val
                485                 490                 495

Trp His Lys Asp Pro Pro Ala Asn Leu Phe Glu Asp Met Asp Leu Asn
            500                 505                 510

Lys Asp Gly Glu Val Pro Pro Glu Glu Phe Ser Thr Phe Ile Lys Ala
        515                 520                 525

Gln Val Ser Glu Gly Lys Gly Arg Leu Met Pro Gly Gln Asp Pro Glu
    530                 535                 540

Lys Thr Ile Gly Asp Met Phe Gln Asn Gln Asp Arg Asn Gln Asp Gly
545                 550                 555                 560
```

-continued

```
Lys Ile Thr Val Asp Glu Leu Lys Leu Lys Ser Asp Glu Asp Glu Glu
            565                 570                 575

Arg Val His Glu Glu Leu
        580
```

(2) INFORMATION FOR SEQ ID NO:2:

(i) SEQUENCE CHARACTERISTICS:
        (A) LENGTH: 2610 base pairs
        (B) TYPE: nucleic acid
        (C) STRANDEDNESS: single
        (D) TOPOLOGY: linear (vii) IMMEDIATE SOURCE:
        (A) LIBRARY: OVARTUT01
        (B) CLONE: 2255114

(xi) SEQUENCE DESCRIPTION: SEQ ID NO:2:

```
CAACTCCCTC GCTCGCCCTC ACTGCCGGCG GTCCCAACTC CAGGCACCAT GTTCCCCGCG     60
GGCCCCCCCA GCCACAGCCT CCTCCGGCTC CCCCTGCTGC AGTTGCTGCT ACTGGTGGTG    120
CAGGCCGTGG GGAGGGGGCT GGGCCGCGCC AGCCCGGCCG GGGGCCCCCT GGAAGATGTG    180
GTCATCGAGA GGTACCACAT CCCCAGGGCC TGTCCCCGGG AAGTGCAGAT GGGGGATTTT    240
GTGCGCTACC ACTACAACGG CACTTTTGAA GATGGCAAGA AGTTTGATTC AAGCTATGAT    300
CGCAACACCT TGGTGGCCAT CGTGGTGGGT GTGGGGCGCC TCATCACTGG CATGGACCGA    360
GGCCTCATGG GCATGTGTGT CAACGAGCGG CGACGCCTCA TTGTGCCTCC CCACCTGGGC    420
TATGGGAGCA TCGGCCTGGC GGGGCTCATT CCACCGGATG CCACCCTCTA CTTCGATGTG    480
GTTCTGCTGG ATGTGTGGAA CAAGGAAGAC ACCGTGCAGG TGAGCACATT GCTGCGCCCG    540
CCCCACTGCC CCCGCATGGT CCAGGACGGC GACTTTGTCC GCTACCACTA CAATGGCACC    600
CTGCTGGACG CACCTCCTT CGACACCAGC TACAGTAAGG GCGGCACTTA TGACACCTAC    660
GTCGGCTCTG GTTGGCTGAT CAAGGGCATG GACCAGGGGC TGCTGGGCAT GTGTCCTGGA    720
GAGAGAAGGA AGATTATCAT CCCTCCATTC CTGGCCTATG GCGAGAAAGG CTATGGGACA    780
GTGATCCCCC CACAGGCCTC GCTGGTCTTT CACGTCCTCC TGATTGACGT GCACAACCCG    840
AAGGACGCTG TCCAGCTAGA GACGCTGGAG CTCCCCCCCG GCTGTGTCCG CAGAGCCGGG    900
GCCGGGGACT TCATGCGCTA CCACTACAAT GGCTCCTTGA TGGACGGCAC CCTCTTCGAT    960
TCCAGCTACT CCCGCAACCA CACCTACAAT ACCTATATCG GCAGGGTTA CATCATCCCC   1020
GGGATGGACC AGGGGCTGCA GGGTGCCTGC ATGGGGAAC GCCGGAGAAT TACCATCCCC   1080
CCGCACCTCG CCTATGGGGA GAATGGAACT GGAGACAAGA TCCCTGGCTC TGCCGTGCTA   1140
ATCTTCAACG TCCATGTCAT TGACTTCCAC AACCCTGCGG ATGTGGTGGA AATCAGGACA   1200
CTGTCCCGGC CATCTGAGAC CTGCAATGAG ACCACCAAGC TTGGGGACTT TGTTCGATAC   1260
CATTACAACT GTTCTTTGCT GGACGGCACC CAGCTGTTCA CCTCGCATGA CTACGGGGCC   1320
CCCCAGGAGG CGACTCTCGG GGCCAACAAG GTGATCGAAG GCCTGGACAC GGGCCTGCAG   1380
GGCATGTGTG TGGGAGAGAG GCGGCAGCTC ATCGTGCCCC CGCACCTGGC CCACGGGGAG   1440
AGTGGAGCCC GGGGAGTCCC AGGCAGTGCT GTGCTGCTGT TGAGGTGGA GCTGGTGTCC   1500
CGGGAGGATG GGCTGCCCAC AGGCTACCTG TTTGTGTGGC ACAAGGACCC TCCTGCCAAC   1560
CTGTTTGAAG ACATGGACCT CAACAAGGAT GGCGAGGTCC CTCCGGAGGA GTTCTCCACC   1620
TTCATCAAGG CTCAAGTGAG TGAGGGCAAA GGACGCCTCA TGCCTGGGCA GGACCCTGAG   1680
AAAACCATAG GAGACATGTT CCAGAACCAG GACCGCAACC AGGACGGCAA GATCACAGTC   1740
```

```
GACGAGCTCA AGCTGAAGTC AGATGAGGAC GAGGAGCGGG TCCACGAGGA GCTCTGAGGG    1800

GCAGGGAGCC TGGCCAGGCC TGAGACACAG AGGCCCACTG CGAGGGGAC AGTGGCGGTG     1860

GGACTGACCT GCTGACAGTC ACCCTCCCTC TGCTGGGATG AGGTCCAGGA GCCAACTAAA    1920

ACAATGGCAG AGGAGACATC TCTGGTGTTC CCACCACCCT AGATGAAAAT CCACAGCACA    1980

GACCTCTACC GTGTTTCTCT TCCATCCCTA AACCACTTCC TTAAAATGTT TGGATTTGCA    2040

AAGCCAATTT GGGGCCTGTG GAGCCTGGGG TTGGATAGGG CCATGGCTGG TCCCCCACCA    2100

TACCTCCCCT CCACATCACT GACACAGCTG AGCTTGTTAT CCATCTCCCC AAACTTTCTC    2160

TTTCTTTGTA CTTCTTGTCA TCCCCACTCC CAGCCCCTAT TCCTCTATGT GACAGCTGGC    2220

TAGGACCCCT CTGCCTTCCT CCCCAATCCT GACTGGCTCC TAGGGAAGGG GAAGGCTCCT    2280

GGAGGGCAGC CCTACCTCTC CCATGCCCTT TGCCCTCCTC CCTCGCCTCC AGTGGAGGCT    2340

GAGCTGACCC TGGGCTGCTG GAGGCCAGAC TGGGCTGTAG TTAGCTTTTC ATCCCTAAAG    2400

AAGGCTTTCC CTAAGGAACC ATAGAAGAGA GGAAGAAAAC AAAGGGCATG TGTGAGGGAA    2460

GCTGCTTGGG TGGGTGTTAG GGCTATGAAA TCTTGGATTT GGGGCTGAGG GGTGGGAGGG    2520

AGGGCAGAGC TCTGCACACT CAAAGGCTAA ACTGGTGTCA GTCCTTTTTT CCTTTGTTCC    2580

AAATAAAAGA TTAAACCAAA AAAAAAAAAA                                     2610

(2) INFORMATION FOR SEQ ID NO:3:

(i) SEQUENCE CHARACTERISTICS:
        (A) LENGTH: 276 amino acids
        (B) TYPE: amino acid
        (C) STRANDEDNESS: single
        (D) TOPOLOGY: linear (vii) IMMEDIATE SOURCE:
        (A) LIBRARY: TMLR3DT01
        (B) CLONE: 292808

(xi) SEQUENCE DESCRIPTION: SEQ ID NO:3:

Met Ala Thr Thr Lys Arg Val Leu Tyr Val Gly Leu Ala Glu Glu
1               5                   10                  15

Val Asp Asp Lys Val Leu His Ala Ala Phe Ile Pro Phe Gly Asp Ile
                20                  25                  30

Thr Asp Ile Gln Ile Pro Leu Asp Tyr Glu Thr Glu Lys His Arg Gly
            35                  40                  45

Phe Ala Phe Val Glu Phe Glu Leu Ala Glu Asp Ala Ala Ala Ala Ile
50                  55                  60

Asp Asn Met Asn Glu Ser Glu Leu Phe Gly Arg Thr Ile Arg Val Asn
65                  70                  75                  80

Leu Ala Lys Pro Met Arg Ile Lys Glu Gly Ser Ser Arg Pro Val Trp
                85                  90                  95

Ser Asp Asp Asp Trp Leu Lys Lys Phe Ser Gly Lys Thr Leu Glu Glu
                100                 105                 110

Asn Lys Glu Glu Glu Gly Ser Glu Pro Pro Lys Ala Glu Thr Gln Glu
        115                 120                 125

Gly Glu Pro Ile Ala Lys Lys Ala Arg Ser Asn Pro Gln Val Tyr Met
130                 135                 140

Asp Ile Lys Ile Gly Asn Lys Pro Ala Gly Arg Ile Gln Met Leu Leu
145                 150                 155                 160

Arg Ser Asp Val Val Pro Met Thr Ala Glu Asn Phe Arg Cys Leu Cys
                165                 170                 175

Thr His Glu Lys Gly Phe Gly Phe Lys Gly Ser Ser Phe His Arg Ile
                180                 185                 190
```

```
Ile Pro Gln Phe Ile Cys Gln Gly Ser Asp Phe Thr Asn His Gly Gly
        195                 200                 205
Thr Arg Gly Leu Arg Arg His Gly Thr Lys Cys Pro Met Ala His Leu
    210                 215                 220
Ala Leu Met Glu Ala Ser Lys Gly Gln Asp Gln His Pro Leu Leu Arg
225                 230                 235                 240
Arg Lys Glu Arg Ala Gln Gln Gly Glu Pro Leu Arg Leu Ile Lys Ala
                245                 250                 255
Ser Pro Leu Asn Leu Leu Arg Gly Lys His Lys Ala Val Gln Tyr Gln
            260                 265                 270
Glu Leu Gly Phe
        275
```

(2) INFORMATION FOR SEQ ID NO:4:

(i) SEQUENCE CHARACTERISTICS:
        (A) LENGTH: 1262 base pairs
        (B) TYPE: nucleic acid
        (C) STRANDEDNESS: single
        (D) TOPOLOGY: linear (vii) IMMEDIATE SOURCE:
        (A) LIBRARY: TMLRDT01
        (B) CLONE: 292808

(xi) SEQUENCE DESCRIPTION: SEQ ID NO:4:

```
ACAGTGGGGA AGAGGACGGG TCGAGTGCTG GCTTCCGGCG GAAAAGCGCG CGAGCAAGAT    60
GGCCACCACC AAGCGCGTCT TGTACGTGGG TGGACTGGCA GAGGAAGTGG ACGACAAAGT   120
TCTTCATGCT GCGTTCATTC CTTTTGGAGA CATCACAGAT ATTCAGATTC CTCTGGATTA   180
TGAAACAGAA AAGCACCGAG GATTTGCTTT TGTTGAATTT GAGTTGGCAG AGGATGCTGC   240
AGCAGCTATC GACAACATGA ATGAATCTGA GCTTTTTGGA CGTACAATTC GTGTCAATTT   300
GGCCAAACCA ATGAGAATTA AGGAAGGCTC TTCCAGGCCA GTTTGGTCAG ATGATGACTG   360
GTTGAAGAAG TTTTCTGGGA AGACGCTTGA AGAGAATAAA GAGGAAGAAG GGTCAGAGCC   420
TCCCAAAGCA GAGACCCAGG AGGGAGAGCC CATTGCTAAA AAGGCCCGCT CAAATCCTCA   480
GGTGTACATG GACATCAAGA TTGGGAACAA GCCGGCTGGC CGCATCCAGA TGCTCCTGCG   540
TTCTGATGTC GTGCCCATGA CAGCAGAGAA TTTCCGCTGC CTGTGCACTC ATGAAAAGGG   600
CTTTGGCTTT AAGGGAAGCA GCTTCCACCG CATCATCCCC CAGTTCATTT GCCAGGGCAG   660
TGATTTCACA AACCACGGTG GCACCAGGGG TCTGCGCAGG CATGGCACTA AGTGTCCCAT   720
GGCACATTTG GCCCTCATGG AGGCCTCAAA AGGGCAGGAC CAGCACCCTC TTCTACGGAG   780
GAAGGAACGG GCACAGCAGG GTGAGCCACT GCGCCTGATC AAGGCATCAC CGTTGAACCT   840
CCTAAGAGGA AAACATAAGG CTGTGCAATA CCAGGAACTG GGATTCTAGG TTGCCCCAGA   900
TACCAAGGCA TCAAAAGCCA GGGGATCCAG AAAAAACAAA GATGGCCAAG AGAGAAACTG   960
GGGGAAAAGC CAAAAGGTTG AGAGCCACAC CATCTAGAAG CTTCCTGCCT GCGGTGCGGC  1020
ACAGAAACAA GGAGAGTCAG CAATTACCAG CCAGCCGAGG TCCTGGAAGC TGACGTAGAG  1080
CTCGTGCCGA CGGCAGACCT GCCGGCCGTG GGAGCCGCGG ACGTCATCTG CAGGGACAGA  1140
AGGGGCAAGG TCTTTTCTGG GGTTCCTGCT GTGTGCAGCT ACTATGGGGT ACCAGGGTGG  1200
GGGATGCCCT GATGAGCACA TTTGTCAAAT AAATGAATGA CAGGAAACCA AGAAAAAAAA  1260
AA                                                                 1262
```

(2) INFORMATION FOR SEQ ID NO:5:

(i) SEQUENCE CHARACTERISTICS:
    (A) LENGTH: 249 amino acids
    (B) TYPE: amino acid
    (C) STRANDEDNESS: single
    (D) TOPOLOGY: linear (vii) IMMEDIATE SOURCE:
    (A) LIBRARY: KIDNNOT09
    (B) CLONE: 1419071

(xi) SEQUENCE DESCRIPTION: SEQ ID NO:5:

```
Met Thr Gln Phe Leu Glu Gln Gly Glu Ala Thr Leu Ser Val Ala Arg
 1               5                  10                  15

Arg Ala Leu Ala Ala Gln Leu Pro Val Leu Pro Arg Ser Glu Val Thr
            20                  25                  30

Phe Leu Ala Pro Val Thr Arg Pro Asp Lys Val Val Cys Val Gly Met
        35                  40                  45

Asn Tyr Val Asp His Cys Lys Glu Gln Asn Val Pro Val Pro Lys Glu
50                  55                  60

Pro Ile Ile Phe Ser Lys Phe Ala Ser Ser Ile Val Gly Pro Tyr Asp
65                  70                  75                  80

Glu Val Val Leu Pro Pro Gln Ser Gln Glu Val Asp Trp Glu Val Glu
            85                  90                  95

Leu Ala Val Val Ile Gly Lys Lys Gly Lys His Ile Lys Ala Thr Asp
            100                 105                 110

Ala Met Ala His Val Ala Gly Phe Thr Val Ala His Asp Val Ser Ala
        115                 120                 125

Arg Asp Trp Gln Met Arg Arg Asn Gly Lys Gln Trp Leu Leu Gly Lys
        130                 135                 140

Thr Phe Asp Thr Phe Cys Pro Leu Gly Pro Ala Leu Val Thr Lys Asp
145                 150                 155                 160

Ser Val Ala Asp Pro His Asn Leu Lys Ile Cys Cys Arg Val Asn Gly
                165                 170                 175

Glu Val Val Gln Ser Ser Asn Thr Asn Gln Met Val Phe Lys Thr Glu
            180                 185                 190

Asp Leu Ile Ala Trp Val Ser Gln Phe Val Thr Phe Tyr Pro Gly Asp
        195                 200                 205

Val Ile Leu Thr Gly Thr Pro Pro Gly Val Gly Val Phe Arg Lys Pro
210                 215                 220

Pro Val Phe Leu Lys Lys Gly Asp Glu Val Gln Cys Glu Ile Glu Glu
225                 230                 235                 240

Leu Gly Val Ile Ile Asn Lys Val Val
                245
```

(2) INFORMATION FOR SEQ ID NO:6:

(i) SEQUENCE CHARACTERISTICS:
    (A) LENGTH: 777 base pairs
    (B) TYPE: nucleic acid
    (C) STRANDEDNESS: single
    (D) TOPOLOGY: linear (vii) IMMEDIATE SOURCE:
    (A) LIBRARY: KIDNNOT09
    (B) CLONE: 1419071

(xi) SEQUENCE DESCRIPTION: SEQ ID NO:6:

```
ATGACGCAGT TCCTAGAGCA GGGAGAGGCC ACCCTCTCAG TGGCAAGAAG AGCCCTGGCT    60

GCCCAGTTGC CAGTCCTACC ACGGTCGGAG GTAACCTTCC TGGCTCCAGT CACACGACCA   120
```

```
GATAAGGTGG TGTGTGTGGG CATGAATTAT GTGGACCACT GCAAAGAACA GAACGTGCCC    180

GTGCCCAAGG AGCCCATCAT CTTCAGCAAG TTTGCCAGCT CCATCGTGGG GCCCTATGAT    240

GAGGTGGTCC TCCCACCACA GAGCCAGGAG GTAGATTGGG AAGTGGAGCT GGCCGTGGTC    300

ATTGGAAAGA AAGGCAAGCA CATCAAGGCC ACAGATGCTA TGGCCCACGT GGCCGGCTTC    360

ACTGTGGCTC ATGACGTGAG TGCTCGTGAC TGGCTAACAA GACGCAATGG GAAACAGTGG    420

CTGCTGGGAA AAACCTTCGA CACCTTCTGC CCNCTGGGCC CTGCCTTGGT GACCAAGGAC    480

AGTGTAGCAG ATCCACACAA CTTAAAGATC TGCTGCCGAG TGAATGGGGA AGTGGTCCAG    540

AGCGGCAACA CCAACCAGAT GGTATTCAAG ACAGAGGACC TGATAGCCTG GGTCTCCCAG    600

TTTGTTACCT TTTACCCAGG GGATGTCATC CTAACTGGGA CCCCCCCAGG TGTCGGTGTA    660

TTCAGGAAAC CTCCTGTCTT TCTCAAGAAG GGGGATGAAG TCCAGTGTGA GATTGAAGAA    720

CTAGGTGTCA TCATCAACAA GGTGGTGTGA TGGCTCCTGC ACAGGCCCTG CACATAG      777
```

(2) INFORMATION FOR SEQ ID NO:7:

(i) SEQUENCE CHARACTERISTICS:
        (A) LENGTH: 581 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 894162

(xi) SEQUENCE DESCRIPTION: SEQ ID NO:7:

```
Met Phe Leu Val Gly Ser Ser His Thr Leu His Arg Val Arg Ile
 1               5                  10                  15

Leu Pro Leu Leu Leu Leu Gln Thr Leu Glu Arg Gly Leu Gly Arg
                20                  25                  30

Ala Ser Pro Ala Gly Ala Pro Leu Glu Asp Val Ile Glu Arg Tyr
            35                  40                  45

His Ile Pro Arg Ala Cys Pro Arg Glu Val Gln Met Gly Asp Phe Val
 50                  55                  60

Arg Tyr His Tyr Asn Gly Thr Phe Glu Asp Gly Lys Lys Phe Asp Ser
65                  70                  75                  80

Ser Tyr Asp Arg Ser Thr Leu Val Ala Ile Val Val Gly Val Gly Arg
                85                  90                  95

Leu Ile Thr Gly Met Asp Arg Gly Leu Met Gly Met Cys Val Asn Glu
            100                 105                 110

Arg Arg Arg Leu Ile Val Pro Pro His Leu Gly Tyr Gly Ser Ile Gly
        115                 120                 125

Val Ala Gly Leu Ile Pro Pro Asp Ala Thr Leu Tyr Phe Asp Val Val
    130                 135                 140

Leu Leu Asp Val Trp Asn Lys Ala Asp Thr Val Gln Ser Thr Ile Leu
145                 150                 155                 160

Leu Arg Pro Pro Tyr Cys Pro Arg Met Val Gln Asn Ser Asp Phe Val
                165                 170                 175

Arg Tyr His Tyr Asn Gly Thr Leu Leu Asp Gly Thr Gly Phe Asp Asn
            180                 185                 190

Ser Tyr Ser Arg Gly Gly Thr Tyr Asp Thr Tyr Ile Gly Ser Gly Trp
        195                 200                 205

Leu Ile Lys Gly Met Asp Gln Gly Leu Leu Gly Met Cys Pro Gly Glu
    210                 215                 220
```

```
Lys Arg Lys Ile Ile Ile Pro Pro Phe Leu Ala Tyr Gly Glu Lys Gly
225                 230                 235                 240

Tyr Gly Thr Val Ile Pro Pro Gln Ala Ser Leu Val Phe Tyr Val Leu
            245                 250                 255

Leu Leu Asp Val His Asn Pro Lys Asp Thr Val Gln Leu Glu Thr Leu
            260                 265                 270

Glu Leu Pro Gln Gly Cys Val Arg Arg Ala Val Ala Gly Asp Phe Met
            275                 280                 285

Arg Tyr His Tyr Asn Gly Ser Leu Met Asp Gly Thr Leu Phe Asp Ser
        290                 295                 300

Ser Tyr Ser Arg Asn His Thr Tyr Asn Thr Tyr Val Gly Gln Gly Tyr
305                 310                 315                 320

Ile Ile Pro Gly Met Asp Gln Gly Leu Gln Gly Ala Cys Ile Gly Glu
                325                 330                 335

Arg Arg Arg Ile Thr Val Pro Pro His Leu Ala Tyr Gly Glu Asn Gly
            340                 345                 350

Thr Gly Asp Lys Ile Pro Gly Ser Ala Val Leu Ile Phe Asp Val His
        355                 360                 365

Val Ile Asp Phe His Asn Pro Ser Asp Pro Val Glu Ile Lys Thr Leu
    370                 375                 380

Ser Arg Pro Pro Glu Asn Cys Asn Glu Thr Ser Lys Ile Gly Asp Phe
385                 390                 395                 400

Ile Arg Tyr His Tyr Asn Cys Ser Leu Leu Asp Gly Thr Arg Leu Phe
            405                 410                 415

Ser Ser His Asp Tyr Glu Ala Pro Gln Glu Ile Thr Leu Gly Ala Asn
            420                 425                 430

Lys Val Ile Glu Gly Leu Asp Arg Gly Leu Gln Gly Met Cys Val Gly
        435                 440                 445

Glu Arg Arg Gln Leu Ile Val Pro Pro His Leu Ala His Gly Glu Asn
450                 455                 460

Gly Ala Arg Gly Val Pro Gly Ser Ala Val Leu Leu Phe Glu Val Glu
465                 470                 475                 480

Leu Val Ser Arg Glu Asp Gly Leu Pro Thr Gly Tyr Leu Phe Val Trp
            485                 490                 495

Tyr Gln Asp Pro Ser Thr Ser Leu Phe Glu Asp Met Asp Leu Asn Lys
            500                 505                 510

Asp Gly Glu Val Pro Pro Glu Glu Phe Ser Ser Phe Ile Lys Ala Gln
        515                 520                 525

Val Asn Glu Gly Lys Gly Arg Leu Met Pro Gly Gln Asp Pro Asp Lys
530                 535                 540

Thr Ile Ser Asp Met Phe Gln Asn Gln Asp Arg Asn Gln Asp Gly Lys
545                 550                 555                 560

Ile Thr Ala Glu Glu Leu Lys Leu Lys Ser Asp Glu Asp Gln Glu Arg
            565                 570                 575

Val His Glu Glu Leu
            580

(2) INFORMATION FOR SEQ ID NO:8:

(i) SEQUENCE CHARACTERISTICS:
        (A) LENGTH: 273 amino acids
        (B) TYPE: amino acid
        (C) STRANDEDNESS: single
        (D) TOPOLOGY: linear (vii) IMMEDIATE SOURCE:
        (A) LIBRARY: GenBank
```

(B) CLONE: 2190533

(xi) SEQUENCE DESCRIPTION: SEQ ID NO:8:

```
Met Pro Met Asp Tyr Gln Thr Glu Lys His Arg Gly Phe Ala Phe Val
 1               5                  10                  15

Glu Phe Glu Glu Val Glu Asp Ala Met Ser Ala Ile Asp Asn Met Asn
                20                  25                  30

Glu Ser Glu Ile Phe Gly Arg Thr Ile Arg Val Asn Val Ala Arg Pro
            35                  40                  45

Val Arg Ile Arg Glu Gly Trp Ser Arg Pro Val Trp Ser Asp Glu Asn
50                  55                  60

Trp Leu Lys Lys Tyr Gly Ser Ala Pro Leu Glu Gly Arg Lys Leu Asp
65                  70                  75                  80

Glu Pro Asp Ile Val Asn Pro Ser Asp Thr Ser Glu Asn Val Glu Asp
                85                  90                  95

Leu Ser Asp Glu Glu Met Arg Thr Lys Lys Gln Lys Arg Asn Leu Pro
            100                 105                 110

Arg Val Phe Phe Asp Ile Arg Ile Gly Asn Gly Asp Ala Gly Arg Ile
        115                 120                 125

Val Met Glu Leu Arg Ser Asp Ile Val Pro Arg Thr Ala Glu Asn Phe
130                 135                 140

Arg Ala Leu Cys Thr Gly Glu Arg Gly Phe Gly Tyr His Asn Cys Cys
145                 150                 155                 160

Phe His Arg Val Ile Pro Gln Phe Met Cys Gln Gly Asp Phe Val
                165                 170                 175

Lys Gly Asp Gly Thr Gly Gly Lys Ser Ile Tyr Gly Arg Lys Phe Asp
            180                 185                 190

Asp Glu Asn Phe Gln Leu Arg His Glu Gly Phe Gly Val Leu Ser Met
        195                 200                 205

Ala Asn Ser Gly Pro Asn Thr Asn Gly Ser Gln Phe Phe Ile Cys Thr
    210                 215                 220

Thr Lys Cys Asp Trp Leu Asp Gly Lys His Val Val Phe Gly Arg Val
225                 230                 235                 240

Val Asp Gly Gln Asn Val Val Lys Lys Met Glu Ser Val Gly Ser Lys
                245                 250                 255

Ser Gly Lys Val Lys Glu Pro Val Ile Ile Ser Arg Cys Gly Glu Leu
            260                 265                 270

Ile
```

(2) INFORMATION FOR SEQ ID NO:9:

(i) SEQUENCE CHARACTERISTICS:
        (A) LENGTH: 237 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1500558

(xi) SEQUENCE DESCRIPTION: SEQ ID NO:9:

```
Met Ile Ile Ser Phe Glu Lys Leu Gly Glu Lys Tyr Lys Ile Ile Asp
 1               5                  10                  15

Leu Asn Leu Asn Ser Ile Lys Gln Lys Ile Gly Asp Ser Leu Asn Ile
                20                  25                  30

Lys Glu Ile Lys Pro Thr Lys Ile Ile Cys Val Gly Leu Asn Tyr Ile
            35                  40                  45
```

-continued

```
Asp His Ala Lys Glu Leu Asn Met Glu Ile Pro Glu Tyr Pro Ile Ile
    50              55                  60
Phe Leu Lys Pro Thr Ser Ala Ile Ile Tyr Asn Glu Asp Tyr Ile Ile
65              70                  75                      80
Arg Pro Arg Ile Ser Lys Arg Val Asp Tyr Glu Val Glu Leu Ala Ile
                85                  90                  95
Val Ile Gly Lys Lys Cys Lys Asn Ile Lys Lys Asp Glu Ala Asn Asp
            100             105                 110
Tyr Ile Met Gly Tyr Thr Ile Leu Asn Asp Val Thr Ala Arg Asp Leu
        115                 120                 125
Gln Gln Lys Asp Gly Gln Trp Thr Arg Ala Lys Ser Phe Asp Thr Phe
    130             135                 140
Cys Pro Ile Gly Pro Arg Ile Val Lys Asp Ile Asp Pro Met Asn Leu
145             150                 155                     160
Asn Ile Glu Cys Arg Val Asn Gly Glu Ile Lys Gln Lys Ser Asn Thr
                165                 170                 175
Lys Asn Met Ile Phe Asp Val Tyr Glu Leu Val Glu Phe Val Ala Ser
            180                 185                 190
Ile Met Thr Leu Tyr Pro Gly Asp Ile Ile Ser Thr Gly Thr Pro Pro
        195             200                 205
Gly Val Gly Glu Leu Lys Ala Gly Asp Val Val Glu Cys Glu Ile Glu
    210             215                 220
Gly Ile Gly Ile Leu Arg Asn Tyr Val Lys Asp Glu Glu
225             230              235
```